(12) United States Patent
Marquis et al.

(10) Patent No.: US 7,479,271 B2
(45) Date of Patent: Jan. 20, 2009

(54) HUMANIZED ANTI-GHRELIN ANTIBODIES

(75) Inventors: David Matthew Marquis, Encinitas, CA (US); Alain Philippe Vasserot, Carlsbad, CA (US); Derrick Ryan Witcher, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 11/815,379

(22) PCT Filed: Feb. 9, 2006

(86) PCT No.: PCT/US2006/004460

§ 371 (c)(1),
(2), (4) Date: Aug. 2, 2007

(87) PCT Pub. No.: WO2006/091381

PCT Pub. Date: Aug. 31, 2006

(65) Prior Publication Data

US 2008/0118498 A1   May 22, 2008

Related U.S. Application Data

(60) Provisional application No. 60/690,313, filed on Jun. 14, 2005, provisional application No. 60/655,685, filed on Feb. 23, 2005.

(51) Int. Cl.
*C07K 16/00* (2006.01)
*C12P 21/08* (2006.01)
*A61K 39/395* (2006.01)
*A61K 39/00* (2006.01)

(52) U.S. Cl. .............. 424/130.1; 530/387.1; 530/387.9; 530/388.24; 424/133.1; 424/145.1

(58) Field of Classification Search ........................ None
See application file for complete search history.

(56) References Cited

FOREIGN PATENT DOCUMENTS

| | | |
|---|---|---|
| EP | 1 197 496 | 4/2002 |
| WO | WO 01/87335 | 11/2001 |
| WO | WO 2004/024183 | * 3/2004 |
| WO | WO 2005/016951 | 2/2005 |

OTHER PUBLICATIONS

Cummings et al., Elevated Plasma Ghrelin Levels in Prader-Willi Syndrome. Nature Medicine, Jul. 2002, vol. 8, pp. 643-644.*
Cummings et al., Elevated Plasma Ghrelin Levels in Prader-Willi Syndrome. Nature Medicine, Jul. 2002, vol. 8, pp. 643-644.*
Moran et al., Ghrelin and Measures of Satiety Are Altered in Polycystic Ovary Syndrome But Not Differentially Affected by Diet Composition. The Journal of Clinical Endocrinology and Metabolism, Jul. 2004, vol. 89, pp. 3337-3344.*
Cigaina et al., Plasma Ghrelin and Gastric Pacing in Morbidly Obese Patients. Metabolism Clinical and Experimental, 2007, vol. 56, pp. 1017-1021.*
Kusaka et al., Metformin, But Not Pioglitazone, decreases Postchallenge Plasma Ghrelin Levels in Type 2 Diabetic Patients: A Possible Role in Weight Stability? Diabetes, Obesity and Metabolism, Published Online: Mar. 18, 2008, pp. 1-8.*
Balint, R., et al., "Antibody Engineering by Parsimonius Mutagenesis," *Gene* 137(1):109-118 (1993).
Hosoda, et al, "Structural Divergence of Human Ghrelin Identification of Multiple Ghrelin-Derived Molecules Produced by Post-Translational Processing," *Journal of Biological Chemistry* 278(1):64-70 (2003).
Nakai, Yoshikatsu, et al., "Plasma levels of active form of ghrelin during oral glucose tolerence test in patients with anorexia nervosa," *European Journal of Endocrinology*, 149(1):R1-R3 (2003).
Patterson, M., et al., "Ghrelin-like Immunoreactivity in Human Plasma," *Society for Neuroscience Abstracts 2003*:ABSTRN028312 (2003).
International Search Report for PCT/US06/004460, completed Jun. 22, 2006.

* cited by examiner

*Primary Examiner*—Phillip Gambel
*Assistant Examiner*—Sharon Wen
(74) *Attorney, Agent, or Firm*—Charles E. Cohen

(57) ABSTRACT

Humanized antibodies, or antigen-binding portions thereof, that preferentially bind acylated ghrelin with respect to unacylated ghrelin, are disclosed. These molecules have high affinity and a slow off rate for acylated ghrelin, and neutralize acylated ghrelin activity. These antibodies, or antigen-binding portions thereof, are useful for neutralizing acylated ghrelin activity, e.g., in a subject suffering from a disorder in which ghrelin activity is detrimental, such as obesity.

12 Claims, 1 Drawing Sheet

SEQUENCE LISTING

<160> NUMBER OF SEQ ID NOS: 43

<210> SEQ ID NO 1
<211> LENGTH: 28
<212> TYPE: PRT
<213> ORGANISM: Homo sapiens

<400> SEQUENCE: 1

Gly Ser Ser Phe Leu Ser Pro Glu His Gln Arg Val Gln Gln Arg Lys
1               5                   10                  15

```
Glu Ser Lys Lys Pro Pro Ala Lys Leu Gln Pro Arg
            20                  25
```

```
<210> SEQ ID NO 2
<211> LENGTH: 134
<212> TYPE: PRT
<213> ORGANISM: Mus sp.

<400> SEQUENCE: 2

Glu Ile Gln Leu Gln Gln Ser Gly Ala Glu Leu Met Lys Pro Gly Ala
1               5                   10                  15

Ser Val Lys Leu Ser Cys Lys Ala Thr Gly Tyr Ile Phe Thr Gly Tyr
            20                  25                  30

Trp Ile Glu Trp Val Lys Gln Arg Pro Gly His Gly Leu Glu Trp Ile
35                  40                  45

Gly Glu Ile Leu Pro Gly Ser Gly Ser Thr Asn Tyr Asn Glu Lys Phe
50                  55                  60

Lys Gly Lys Ala Thr Phe Thr Ala Asp Thr Ser Ser Asn Thr Ala Asn
65                  70                  75                  80

Met Gln Leu Ser Ser Leu Thr Thr Glu Asp Ser Ala Ile Tyr Tyr Cys
            85                  90                  95

Ala Arg Tyr Pro Gln Phe Arg Leu Arg Arg Glu Arg Ile Ala Tyr Trp
            100                 105                 110

Gly Gln Gly Thr Leu Val Thr Val Ser Val Ala Lys Thr Thr Pro Pro
115                 120                 125

Ser Val Tyr Pro Leu Ala
130
```

```
<210> SEQ ID NO 3
<211> LENGTH: 112
<212> TYPE: PRT
<213> ORGANISM: Mus sp.

<400> SEQUENCE: 3

Asp Leu Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
35                  40                  45

Lys Leu Leu Ile Tyr Leu Ala Ser Asn Leu Glu Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
            85                  90                  95

Glu Leu Pro Tyr Thr Phe Gly Ala Gly Thr Lys Leu Glu Leu Lys Arg
            100                 105                 110
```

```
<210> SEQ ID NO 4
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa at position 8 = Thr or Leu
<220> FEATURE:
<221> NAME/KEY: MISC_FEATURE
<222> LOCATION: (9)..(9)
```

```
<223> OTHER INFORMATION: Xaa at position 9 = Leu, Gly, or Ser
<220> FEATURE:
<221> NAME/KEY: MISC_FEATURE
<222> LOCATION: (10)..(10)
<223> OTHER INFORMATION: Xaa at position 10 = Gly or Asp

<400> SEQUENCE: 4

Arg Ala Ser Lys Ser Val Ser Xaa Xaa Xaa Tyr Ser Tyr Met His
1               5                   10                  15

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 = Phe or Leu

<400> SEQUENCE: 5

Xaa Ala Ser Asn Leu Glu Ser
1               5

<210> SEQ ID NO 6
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa at position 4 = Val or Ile

<400> SEQUENCE: 6

Gln His Ser Xaa Glu Glu Pro Tyr Thr
1               5

<210> SEQ ID NO 7
<211> LENGTH: 10
<212> TYPE: PRT
<213> ORGANISM: Homo sapiens

<400> SEQUENCE: 7

Gly Tyr Ile Phe Thr Gly Tyr Trp Ile Glu
1               5                   10

<210> SEQ ID NO 8
<211> LENGTH: 17
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa at position 2 = Leu or Ile
<220> FEATURE:
<221> NAME/KEY: MISC_FEATURE
<222> LOCATION: (8)..(8)
<223> OTHER INFORMATION: Xaa at position 8 = Thr or Ser

<400> SEQUENCE: 8

Asp Xaa Leu Pro Gly Ser Gly Xaa Pro Asn Tyr Asn Glu Lys Phe Lys
1               5                   10                  15

Gly

<210> SEQ ID NO 9
<211> LENGTH: 13
<212> TYPE: PRT
<213> ORGANISM: Homo sapiens
<220> FEATURE:
```

```
<221> NAME/KEY: MISC_FEATURE
<222> LOCATION: (3)..(3)
<223> OTHER INFORMATION: Xaa at position 3 = Ile or Gln
<220> FEATURE:
<221> NAME/KEY: MISC_FEATURE
<222> LOCATION: (6)..(6)
<223> OTHER INFORMATION: Xaa at position 6 = Pro or Leu
<220> FEATURE:
<221> NAME/KEY: MISC_FEATURE
<222> LOCATION: (13)..(13)
<223> OTHER INFORMATION: Xaa at position 13 = Tyr or Glu

<400> SEQUENCE: 9

Tyr Pro Xaa Phe Arg Xaa Arg Thr Glu Arg Ile Ala Xaa
1               5                   10

<210> SEQ ID NO 10
<211> LENGTH: 111
<212> TYPE: PRT
<213> ORGANISM: Homo sapiens

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Leu
            20                  25                  30

Gly Tyr Ser Tyr Met His Trp Tyr Gln Gln Lys Pro Gly Gln Pro Pro
35                  40                  45

Lys Leu Leu Ile Tyr Phe Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Val
            85                  90                  95

Glu Glu Pro Tyr Thr Phe Gly Gln Gly Thr Lys Leu Glu Ile Lys
        100                 105                 110

<210> SEQ ID NO 11
<211> LENGTH: 122
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Ile Phe Thr Gly Tyr
            20                  25                  30

Trp Ile Glu Trp Val Arg Gln Ala Pro Gly Gln Gly Leu Glu Trp Met
35                  40                  45

Gly Asp Leu Leu Pro Gly Ser Gly Thr Pro Asn Tyr Asn Glu Lys Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Tyr Pro Gln Phe Arg Pro Arg Thr Glu Arg Ile Ala Tyr Trp
        100                 105                 110

Gly Gln Gly Thr Leu Val Thr Val Ser Ser
115                 120
```

```
<210> SEQ ID NO 12
<211> LENGTH: 15
<212> TYPE: PRT
<213> ORGANISM: Homo sapiens

<400> SEQUENCE: 12

Arg Ala Ser Lys Ser Val Ser Thr Leu Gly Tyr Ser Tyr Met His
1               5                   10                  15

<210> SEQ ID NO 13
<211> LENGTH: 15
<212> TYPE: PRT
<213> ORGANISM: Homo sapiens

<400> SEQUENCE: 13

Arg Ala Ser Lys Ser Val Ser Thr Gly Gly Tyr Ser Tyr Met His
1               5                   10                  15

<210> SEQ ID NO 14
<211> LENGTH: 15
<212> TYPE: PRT
<213> ORGANISM: Homo sapiens

<400> SEQUENCE: 14

Arg Ala Ser Lys Ser Val Ser Leu Ser Asp Tyr Ser Tyr Met His
1               5                   10                  15

<210> SEQ ID NO 15
<211> LENGTH: 15
<212> TYPE: PRT
<213> ORGANISM: Homo sapiens

<400> SEQUENCE: 15

Arg Ala Ser Lys Ser Val Ser Leu Ser Gly Tyr Ser Tyr Met His
1               5                   10                  15

<210> SEQ ID NO 16
<211> LENGTH: 15
<212> TYPE: PRT
<213> ORGANISM: Homo sapiens

<400> SEQUENCE: 16

Arg Ala Ser Lys Ser Val Ser Leu Leu Gly Tyr Ser Tyr Met His
1               5                   10                  15

<210> SEQ ID NO 17
<211> LENGTH: 7
<212> TYPE: PRT
<213> ORGANISM: Homo sapiens

<400> SEQUENCE: 17

Phe Ala Ser Asn Leu Glu Ser
1               5

<210> SEQ ID NO 18
<211> LENGTH: 7
<212> TYPE: PRT
<213> ORGANISM: Homo sapiens

<400> SEQUENCE: 18

Leu Ala Ser Asn Leu Glu Ser
1               5

<210> SEQ ID NO 19
<211> LENGTH: 9
```

```
<212> TYPE: PRT
<213> ORGANISM: Homo sapiens

<400> SEQUENCE: 19

Gln His Ser Val Glu Glu Pro Tyr Thr
1               5

<210> SEQ ID NO 20
<211> LENGTH: 9
<212> TYPE: PRT
<213> ORGANISM: Homo sapiens

<400> SEQUENCE: 20

Gln His Ser Ile Glu Glu Pro Tyr Thr
1               5

<210> SEQ ID NO 21
<211> LENGTH: 17
<212> TYPE: PRT
<213> ORGANISM: Homo sapiens

<400> SEQUENCE: 21

Asp Leu Leu Pro Gly Ser Gly Thr Pro Asn Tyr Asn Glu Lys Phe Lys
1               5                   10                  15

Gly

<210> SEQ ID NO 22
<211> LENGTH: 17
<212> TYPE: PRT
<213> ORGANISM: Homo sapiens

<400> SEQUENCE: 22

Asp Ile Leu Pro Gly Ser Gly Thr Pro Asn Tyr Asn Glu Lys Phe Lys
1               5                   10                  15

Gly

<210> SEQ ID NO 23
<211> LENGTH: 17
<212> TYPE: PRT
<213> ORGANISM: Homo sapiens

<400> SEQUENCE: 23

Asp Leu Leu Pro Gly Ser Gly Thr Pro Asn Tyr Asn Glu Lys Phe Lys
1               5                   10                  15

Gly

<210> SEQ ID NO 24
<211> LENGTH: 17
<212> TYPE: PRT
<213> ORGANISM: Homo sapiens

<400> SEQUENCE: 24

Asp Ile Leu Pro Gly Ser Gly Thr Pro Asn Tyr Asn Glu Lys Phe Lys
1               5                   10                  15

Gly

<210> SEQ ID NO 25
<211> LENGTH: 13
<212> TYPE: PRT
<213> ORGANISM: Homo sapiens

<400> SEQUENCE: 25
```

```
Tyr Pro Gln Phe Arg Pro Arg Thr Glu Arg Ile Ala Tyr
1               5                   10

<210> SEQ ID NO 26
<211> LENGTH: 13
<212> TYPE: PRT
<213> ORGANISM: Homo sapiens

<400> SEQUENCE: 26

Tyr Pro Ile Phe Arg Leu Arg Thr Glu Arg Ile Ala Glu
1               5                   10

<210> SEQ ID NO 27
<211> LENGTH: 13
<212> TYPE: PRT
<213> ORGANISM: Homo sapiens

<400> SEQUENCE: 27

Tyr Pro Gln Phe Arg Leu Arg Thr Glu Arg Ile Ala Glu
1               5                   10

<210> SEQ ID NO 28
<211> LENGTH: 13
<212> TYPE: PRT
<213> ORGANISM: Homo sapiens

<400> SEQUENCE: 28

Tyr Pro Ile Phe Arg Pro Arg Thr Glu Arg Ile Ala Tyr
1               5                   10

<210> SEQ ID NO 29
<211> LENGTH: 122
<212> TYPE: PRT
<213> ORGANISM: Homo sapiens

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Ile Phe Thr Gly Tyr
            20                  25                  30

Trp Ile Glu Trp Val Arg Gln Ala Pro Gly Gln Gly Leu Glu Trp Met
35                  40                  45

Gly Asp Ile Leu Pro Gly Ser Gly Thr Pro Asn Tyr Asn Glu Lys Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Tyr Pro Ile Phe Arg Leu Arg Thr Glu Arg Ile Ala Glu Trp
            100                 105                 110

Gly Gln Gly Thr Leu Val Thr Val Ser Ser
115                 120

<210> SEQ ID NO 30
<211> LENGTH: 111
<212> TYPE: PRT
<213> ORGANISM: Homo sapiens

<400> SEQUENCE: 30

Asp Ile Val Met Thr Gln Ser Pro Asp Ser Leu Ala Val Ser Leu Gly
1               5                   10                  15
```

```
Glu Arg Ala Thr Ile Asn Cys Arg Ala Ser Lys Ser Val Ser Thr Gly
            20                  25                  30

Gly Tyr Ser Tyr Met His Trp Tyr Gln Gln Lys Pro Gly Gln Pro Pro
 35                  40                  45

Lys Leu Leu Ile Tyr Phe Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Ile
             85                  90                  95

Glu Glu Pro Tyr Thr Phe Gly Gln Gly Thr Lys Leu Glu Ile Lys
        100                 105                 110
```

<210> SEQ ID NO 31
<211> LENGTH: 122
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ala
 1               5                  10                  15

Ser Val Lys Val Ser Cys Lys Ala Thr Gly Tyr Ile Phe Thr Gly Tyr
            20                  25                  30

Trp Ile Glu Trp Val Arg Gln Ala Pro Gly Gln Gly Leu Glu Trp Met
 35                  40                  45

Gly Asp Leu Leu Pro Gly Ser Gly Ser Pro Asn Tyr Asn Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
             85                  90                  95

Ala Arg Tyr Pro Ile Phe Arg Leu Arg Thr Glu Arg Ile Ala Glu Trp
        100                 105                 110

Gly Gln Gly Thr Leu Val Thr Val Ser Ser
115                 120
```

<210> SEQ ID NO 32
<211> LENGTH: 111
<212> TYPE: PRT
<213> ORGANISM: Homo sapiens

<400> SEQUENCE: 32

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Leu Ser
            20                  25                  30

Asp Tyr Ser Tyr Met His Trp Tyr Gln Gln Lys Pro Gly Gln Pro Pro
 35                  40                  45

Lys Leu Leu Ile Tyr Phe Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Ile
             85                  90                  95

Glu Glu Pro Tyr Thr Phe Gly Gln Gly Thr Lys Leu Glu Ile Lys
        100                 105                 110
```

```
<210> SEQ ID NO 33
<211> LENGTH: 122
<212> TYPE: PRT
<213> ORGANISM: Homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Ile Phe Thr Gly Tyr
                20                  25                  30

Trp Ile Glu Trp Val Arg Gln Ala Pro Gly Gln Gly Leu Glu Trp Met
35                  40                  45

Gly Asp Leu Leu Pro Gly Ser Gly Thr Pro Asn Tyr Asn Glu Lys Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Pro Gln Phe Arg Pro Arg Thr Glu Arg Ile Ala Tyr Trp
            100                 105                 110

Gly Gln Gly Thr Leu Val Thr Val Ser Ser
115                 120

<210> SEQ ID NO 34
<211> LENGTH: 111
<212> TYPE: PRT
<213> ORGANISM: Homo sapiens

<400> SEQUENCE: 34

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Leu Ser
                20                  25                  30

Gly Tyr Ser Tyr Met His Trp Tyr Gln Gln Lys Pro Gly Gln Pro Pro
35                  40                  45

Lys Leu Leu Ile Tyr Phe Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Ile
                85                  90                  95

Glu Glu Pro Tyr Thr Phe Gly Gln Gly Thr Lys Leu Glu Ile Lys
            100                 105                 110

<210> SEQ ID NO 35
<211> LENGTH: 122
<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Ile Phe Thr Gly Tyr
                20                  25                  30

Trp Ile Glu Trp Val Arg Gln Ala Pro Gly Gln Gly Leu Glu Trp Met
35                  40                  45

Gly Asp Ile Leu Pro Gly Ser Gly Ser Pro Asn Tyr Asn Glu Lys Phe
```

```
                    50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Tyr Pro Ile Phe Arg Leu Arg Thr Glu Arg Ile Ala Glu Trp
            100                 105                 110

Gly Gln Gly Thr Leu Val Thr Val Ser Ser
115                 120

<210> SEQ ID NO 36
<211> LENGTH: 122
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
 1               5                  10                  15

Ser Val Lys Val Ser Cys Lys Ala Thr Gly Tyr Ile Phe Thr Gly Tyr
                20                  25                  30

Trp Ile Glu Trp Val Arg Gln Ala Pro Gly Gln Gly Leu Glu Trp Met
 35                  40                  45

Gly Asp Ile Leu Pro Gly Ser Gly Ser Pro Asn Tyr Asn Glu Lys Phe
 50                  55                  60

Lys Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Tyr Pro Ile Phe Arg Pro Arg Thr Glu Arg Ile Ala Tyr Trp
            100                 105                 110

Gly Gln Gly Thr Leu Val Thr Val Ser Ser
115                 120

<210> SEQ ID NO 37
<211> LENGTH: 111
<212> TYPE: PRT
<213> ORGANISM: Homo sapiens

<400> SEQUENCE: 37

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Leu Leu
                20                  25                  30

Gly Tyr Ser Tyr Met His Trp Tyr Gln Gln Lys Pro Gly Gln Pro Pro
 35                  40                  45

Lys Leu Leu Ile Tyr Phe Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Val
                 85                  90                  95

Glu Glu Pro Tyr Thr Phe Gly Gln Gly Thr Lys Leu Glu Ile Lys
            100                 105                 110

<210> SEQ ID NO 38
<211> LENGTH: 111
<212> TYPE: PRT
```

<213> ORGANISM: Homo sapiens

<400> SEQUENCE: 38

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Leu Leu
            20                  25                  30

Gly Tyr Ser Tyr Met His Trp Tyr Gln Gln Lys Pro Gly Gln Pro Pro
35                  40                  45

Lys Leu Leu Ile Tyr Phe Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Ile
                85                  90                  95

Glu Glu Pro Tyr Thr Phe Gly Gln Gly Thr Lys Leu Glu Ile Lys
            100                 105                 110
```

<210> SEQ ID NO 39
<211> LENGTH: 111
<212> TYPE: PRT
<213> ORGANISM: Homo sapiens

<400> SEQUENCE: 39

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Leu Ser
            20                  25                  30

Gly Tyr Ser Tyr Met His Trp Tyr Gln Gln Lys Pro Gly Gln Pro Pro
35                  40                  45

Lys Leu Leu Ile Tyr Phe Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Val
                85                  90                  95

Glu Glu Pro Tyr Thr Phe Gly Gln Gly Thr Lys Leu Glu Ile Lys
            100                 105                 110
```

<210> SEQ ID NO 40
<211> LENGTH: 111
<212> TYPE: PRT
<213> ORGANISM: Homo sapiens

<400> SEQUENCE: 40

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Leu
            20                  25                  30

Gly Tyr Ser Tyr Met His Trp Tyr Gln Gln Lys Pro Gly Gln Pro Pro
35                  40                  45

Lys Leu Leu Ile Tyr Phe Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Ile
                85                  90                  95
```

Glu Glu Pro Tyr Thr Phe Gly Gln Gly Thr Lys Leu Glu Ile Lys
            100                 105                 110

<210> SEQ ID NO 41
<211> LENGTH: 111
<212> TYPE: PRT
<213> ORGANISM: Homo sapiens

<400> SEQUENCE: 41

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Thr Gly
            20                  25                  30

Gly Tyr Ser Tyr Met His Trp Tyr Gln Gln Lys Pro Gly Gln Pro Pro
35                  40                  45

Lys Leu Leu Ile Tyr Leu Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Val
            85                  90                  95

Glu Glu Pro Tyr Thr Phe Gly Gln Gly Thr Lys Leu Glu Ile Lys
            100                 105                 110

<210> SEQ ID NO 42
<211> LENGTH: 111
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa at position 31 = Thr or Leu
<220> FEATURE:
<221> NAME/KEY: MISC_FEATURE
<222> LOCATION: (32)..(32)
<223> OTHER INFORMATION: Xaa at position 32 = Leu, Gly, or Ser
<220> FEATURE:
<221> NAME/KEY: MISC_FEATURE
<222> LOCATION: (33)..(33)
<223> OTHER INFORMATION: Xaa at position 33 = Gly or Asp
<220> FEATURE:
<221> NAME/KEY: MISC_FEATURE
<222> LOCATION: (54)..(54)
<223> OTHER INFORMATION: Xaa at position 54 = Phe or Leu
<220> FEATURE:
<221> NAME/KEY: MISC_FEATURE
<222> LOCATION: (96)..(96)
<223> OTHER INFORMATION: Xaa at position 96 = Val or Ile

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Arg Ala Ser Lys Ser Val Ser Xaa Xaa
            20                  25                  30

Xaa Tyr Ser Tyr Met His Trp Tyr Gln Gln Lys Pro Gly Gln Pro Pro
35                  40                  45

Lys Leu Leu Ile Tyr Xaa Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Xaa
            85                  90                  95

```
Glu Glu Pro Tyr Thr Phe Gly Gln Gly Thr Lys Leu Glu Ile Lys
        100                 105                 110

<210> SEQ ID NO 43
<211> LENGTH: 122
<212> TYPE: PRT
<213> ORGANISM: Homo sapiens
<220> FEATURE:
<221> NAME/KEY: MISC_FEATURE
<222> LOCATION: (51)..(51)
<223> OTHER INFORMATION: Xaa at position 51 = Leu or Ile
<220> FEATURE:
<221> NAME/KEY: MISC_FEATURE
<222> LOCATION: (57)..(57)
<223> OTHER INFORMATION: Xaa at position 57 = Thr or Ser
<220> FEATURE:
<221> NAME/KEY: MISC_FEATURE
<222> LOCATION: (101)..(101)
<223> OTHER INFORMATION: Xaa at position 101 = Ile or Gln
<220> FEATURE:
<221> NAME/KEY: MISC_FEATURE
<222> LOCATION: (104)..(104)
<223> OTHER INFORMATION: Xaa at position 104 = Pro or Leu
<220> FEATURE:
<221> NAME/KEY: MISC_FEATURE
<222> LOCATION: (111)..(111)
<223> OTHER INFORMATION: Xaa at position 111 = Tyr or Glu

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Thr Gly Tyr Ile Phe Thr Gly Tyr
            20                  25                  30

Trp Ile Glu Trp Val Arg Gln Ala Pro Gly Gln Gly Leu Glu Trp Met
35                  40                  45

Gly Asp Xaa Leu Pro Gly Ser Gly Xaa Pro Asn Tyr Asn Glu Lys Phe
50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Tyr Pro Xaa Phe Arg Xaa Arg Thr Glu Arg Ile Ala Xaa Trp
            100                 105                 110

Gly Gln Gly Thr Leu Val Thr Val Ser Ser
115                 120
```

HUMANIZED ANTI-GHRELIN ANTIBODIES

This application is a §371 national phase filing of PCT/US2006/004460, filed Feb. 9, 2006, which claims the benefit of Provisional Application No. 60/655,685, filed Feb. 23, 2005, and Provisional Application No. 60/690,313, filed Jun. 14, 2005.

BACKGROUND OF THE INVENTION

1. Field of the Invention

The present invention is in the field of medicine, particularly in the field of monoclonal antibodies against human ghrelin useful for treatment of obesity and obesity-related disorders, including non-insulin dependent diabetes mellitus, Prader-Willi syndrome, hyperphagia, and impaired satiety. More specifically, the present invention relates to humanized, affinity matured monoclonal antibodies and antigen-binding portions thereof that preferentially bind acylated human ghrelin with respect to unacylated human ghrelin.

2. Description of Related Art

Obesity is a complex, chronic disease characterized by excessive accumulation of body fat, and has a strong familial component. Obesity increases the risk of illness from about 30 serious medical conditions, including osteoarthritis, Type II diabetes, hypertension, cancer, and cardiovascular disease, and is associated with increases in deaths from all causes. Additionally, obesity is associated with depression, and can further affect the quality of life through limited mobility and decreased physical endurance.

Human ghrelin is a recently identified peptide hormone having the amino acid sequence GSSFLSPE-HQRVQQRKESKKPPAKLQPR (SEQ ID NO:1) that, when acylated at the serine at amino acid position three ($Ser^3$) with an n-octanoyl group ("C8" or "C8 acylated ghrelin"), binds the growth hormone secretagogue receptor (GHS-R1a), resulting in release of growth hormone (Kojima et al., *Nature* 402:656-660, 1999).

Ghrelin has been demonstrated to lead to fat deposition when administered to mice (Tschop et al., *Nature* 407:908-913, 2000). Ghrelin is synthesized primarily in the stomach, and its levels increase during food deprivation in animals (Kojima et al., *Nature* 402:656-660, 1999) and peak prior to eating in humans (Cummings et al., *NEJM*, 346:1623-1630, 2002). Recently, it has been shown that persons who underwent gastric bypass surgery and lost up to 36% of their body weight had greatly reduced ghrelin levels, with loss of pre-meal peaks in ghrelin secretion. Persons with Prader-Willi syndrome, a genetic disorder that causes severe obesity with uncontrollable appetite, have extremely high levels of ghrelin (Cummings et al., *NEJM*, 346:1623-1630, 2002). These observations indicate that ghrelin plays a key role in motivating feeding.

In addition to its role in eating disorders, ghrelin has also been shown to have a proliferative effect in the HepG2 hepatoma cell line (Murata et al., *J. Biol. Chem.*, 277:5667-5674, 2002) and in prostate cancer cell lines (Jeffrey et al., *J. Endocrinol.*, 172:7-11, 2002; Yeh et al. (*Clin. Cancer Res.*, 11(23):8295-8303, 2005). The growth of other cell types including, for example, H9c2 cardiomyocytes, pancreatic adenocarcinoma, adrenal cells, pituitary somatotroph cells, adipocytes, osteoblastic cells, breast cancer cell lines, etc., is also enhanced by ghrelin (discussed in Yeh et al., supra).

International application PCT/US2004/014537 (WO 2005/016951) discloses the Fab portion of a murine monoclonal antibody to the N-terminal end of acylated ghrelin, designated therein as Fab 1111. This Fab, which binds between amino acids 1 and 8 of C8 acylated human ghrelin with a $K_d$ of 1.04 nM, is a murine sequence referred to herein as a C2 Fab. The amino acid sequences of the heavy chain and light chain of C2 murine Fab 1111 are shown below, with the CDR regions underlined:

---

C2 Ghrelin Murine Fab 1111

Heavy Chain (SEQ ID NO:2)
EIQLQQSGAELMKPGASVKLSCKAT<u>GYIFTGYWIE</u>WVKQRPGHGLEWIG<u>E</u>

<u>ILPGSGSTNYNEKFKG</u>KATFTADTSSNTANMQLSSLTTEDSAIYYCAR<u>YP</u>

<u>QFRLRRERIAY</u>WGQGTLVTVSVAKTTPPSVYPLA

Light Chain (SEQ ID NO:3)
DLVLTQSPASLAVSLGQRATISC<u>RASKSVSTSGYSYMH</u>WYQQKPGQPPKL LIY<u>LASNLES</u>GVPARFSGSGSGTDFTLNIHPVEEEDAATYYC<u>QHSRELPY</u>

<u>TFGAGTKLELKR</u>.

---

There is a pressing therapeutic need for a means to treat obesity and obesity-related disorders. Due to its potential role in inducing feeding, ghrelin is a desirable target for therapeutic intervention. In particular, a monoclonal antibody against ghrelin that preferentially binds the acylated form of ghrelin with respect to the unacylated form of ghrelin may provide such a therapy. Of particular importance therapeutically is a humanized, affinity-optimized form of such a monoclonal antibody. Such an anti-ghrelin antibody may be useful for the treatment of obesity, including morbid obesity, and related disorders including, for example, Type II non-insulin dependent diabetes mellitus (NIDDM), Prader-Willi syndrome, hyperphagia, and impaired satiety.

Therapeutically beneficial antibodies that bind to the epitope recognized by the C2 antibody will desirably be stable in solution, display favorable pharmacokinetics, and possess improved affinity toward an epitope formed by amino acids 1 to 8 of acylated ghrelin. Therefore, there is a need in the art for humanized antibodies having characteristics similar to or better than C2 murine Fab 1111, which will be therapeutically efficacious in humans, with few or no side effects.

SUMMARY OF THE INVENTION

The present invention provides humanized, affinity matured antibodies, or antigen-binding portions thereof, that specifically bind acylated human ghrelin, i.e., human ghrelin O-acylated with n-octanoic acid at the third amino acid residue from its amino terminus, wherein the antibodies or antigen-binding portions thereof comprise a light chain and a heavy chain, and wherein: (a) the light chain is comprised of (i) a light chain CDR (Complementarity Determining Region) 1 having the amino acid sequence shown in SEQ ID NO:4; (ii) a light chain CDR2 having the amino acid sequence shown in SEQ ID NO:5; and (iii) a light chain CDR3 having the amino acid sequence shown in SEQ ID NO:6; and (b) the heavy chain is comprised of (i) a heavy chain CDR1 having the amino acid sequence shown in SEQ ID NO:7; (ii) a heavy chain CDR2 having the amino acid sequence shown in SEQ ID NO:8; and (iii) a heavy chain CDR3 having the amino acid sequence shown in SEQ ID NO:9.

More particularly, in one aspect, the present invention provides a humanized, affinity matured monoclonal antibody, or antigen-binding portion thereof, against acylated human ghrelin, that preferentially binds acylated human ghrelin with respect to unacylated human ghrelin and that exhibits an affinity for acylated human ghrelin equal to or greater than that of C2 murine Fab 1111 having a heavy chain variable region comprising a peptide with the sequence shown in SEQ ID NO:2 and a light chain variable region comprising a peptide with the sequence shown in SEQ ID NO:3.

Such humanized, affinity matured monoclonal antibodies or antigen-binding portions thereof exhibit dissociation constants, $K_d$s, in the range of from about $10^{-8}$ M to about $5 \times 10^{-10}$ M, more preferably from about $10^{-11}$ M to about 1 pM.

In another aspect, the humanized, affinity matured monoclonal antibody or antigen-binding portion thereof of is selected from the group consisting of a Fab fragment, a monovalent fragment consisting of the VL, VH, CL, and CH 1 domains, a F(ab')$_2$ fragment, a bivalent fragment comprising two Fab fragments linked by a disulfide bridge at the hinge region, an Fd fragment consisting of the VH and CH1 domains, and an Fv fragment consisting of the VL and VH domains of a single arm of an antibody, a dAb fragment consisting of a VH domain, or a scFv fragment.

In another aspect, the present invention provides humanized, affinity matured monoclonal antibodies or antigen-binding portions thereof comprising peptides having the following amino acid sequences:

a) SEQ ID NO:12 located at CDR1 of the light chain variable region (LCVR); SEQ ID NO:17 located at CDR2 of the LCVR; SEQ ID NO:19 located at CDR3 of the LCVR; SEQ ID NO:7 located at CDR1 of the heavy chain variable region (HCVR); SEQ ID NO:21 located at CDR2 of the HCVR; and SEQ ID NO:25 located at CDR3 of the HCVR;

b) SEQ ID NO:12 located at CDR1 of the LCVR; SEQ ID NO:17 located at CDR2 of the LCVR; SEQ ID NO:19 located at CDR3 of the LCVR; SEQ ID NO:7 located at CDR1 of the HCVR; SEQ ID NO:22 located at CDR2 of the HCVR; and SEQ ID NO:26 located at CDR3 of the HCVR;

c) SEQ ID NO:13 located at CDR1 of the LCVR; SEQ ID NO:17 located at CDR2 of the LCVR; SEQ ID NO:20 located at CDR3 of the LCVR; SEQ ID NO:7 located at CDR1 of the HCVR; SEQ ID NO:23 located at CDR2 of the HCVR; and SEQ ID NO:26 located at CDR3 of the HCVR;

d) SEQ ID NO:14 located at CDR1 of the LCVR; SEQ ID NO:17 located at CDR2 of the LCVR; SEQ ID NO:20 located at CDR3 of the LCVR; SEQ ID NO:7 located at CDR1 of the HCVR; SEQ ID NO:22 located at CDR2 of the HCVR; and SEQ ID NO:27 located at CDR3 of the HCVR;

e) SEQ ID NO:15 located at CDR1 of the LCVR; SEQ ID NO:17 located at CDR2 of the LCVR; SEQ ID NO:20 located at CDR3 of the LCVR; SEQ ID NO:7 located at CDR1 of the HCVR; SEQ ID NO:24 located at CDR2 of the HCVR; and SEQ ID NO:26 located at CDR3 of the HCVR;

f) SEQ ID NO:12 located at CDR1 of the LCVR; SEQ ID NO:17 located at CDR2 of the LCVR; SEQ ID NO:19 located at CDR3 of the LCVR; SEQ ID NO:7 located at CDR1 of the HCVR; SEQ ID NO:24 located at CDR2 of the HCVR; and SEQ ID NO:28 located at CDR3 of the HCVR;

g) SEQ ID NO:16 located at CDR1 of the LCVR; SEQ ID NO:17 located at CDR2 of the LCVR; SEQ ID NO:19 located at CDR3 of the LCVR; SEQ ID NO:7 located at CDR1 of the HCVR; SEQ ID NO:24 located at CDR2 of the HCVR; and SEQ ID NO:28 located at CDR3 of the HCVR;

h) SEQ ID NO:16 located at CDR1 of the LCVR; SEQ ID NO:17 located at CDR2 of the LCVR; SEQ ID NO:20 located at CDR3 of the LCVR; SEQ ID NO:7 located at CDR1 of the HCVR; SEQ ID NO:24 located at CDR2 of the HCVR; and SEQ ID NO:26 located at CDR3 of the HCVR;

i) SEQ ID NO:15 located at CDR1 of the LCVR; SEQ ID NO:17 located at CDR2 of the LCVR; SEQ ID NO:19 located at CDR3 of the LCVR; SEQ ID NO:7 located at CDR1 of the HCVR; SEQ ID NO:24 located at CDR2 of the HCVR; and SEQ ID NO:28 located at CDR3 of the HCVR;

j) SEQ ID NO:12 located at CDR1 of the LCVR; SEQ ID NO:17 located at CDR2 of the LCVR; SEQ ID NO:20 located at CDR3 of the LCVR; SEQ ID NO:7 located at CDR1 of the HCVR; SEQ ID NO:23 located at CDR2 of the HCVR; and SEQ ID NO:26 located at CDR3 of the HCVR; or k) SEQ ID NO:13 located at CDR1 of the LCVR; SEQ ID NO:18 located at CDR2 of the LCVR; SEQ ID NO:19 located at CDR3 of the LCVR; SEQ ID NO:7 located at CDR1 of the HCVR; SEQ ID NO:24 located at CDR2 of the HCVR; and SEQ ID NO:26 located at CDR3 of the HCVR.

In yet another aspect, the present invention provides a humanized, affinity matured monoclonal antibody or antigen-binding portion thereof wherein:

a) the light chain variable region comprises a peptide with the sequence shown in SEQ ID NO:10 and the heavy chain variable region comprises a peptide with the sequence shown in SEQ ID NO:11;

b) the light chain variable region comprises a peptide with the sequence shown in SEQ ID NO:10 and the heavy chain variable region comprises a peptide with the sequence shown in SEQ ID NO:29;

c) the light chain variable region comprises a peptide with the sequence shown in SEQ ID NO:30 and the heavy chain variable region comprises a peptide with the sequence shown in SEQ ID NO:31;

d) the light chain variable region comprises a peptide with the sequence shown in SEQ ID NO:32 and the heavy chain variable region comprises a peptide with the sequence shown in SEQ ID NO:33;

e) the light chain variable region comprises a peptide with the sequence shown in SEQ ID NO:34 and the heavy chain variable region comprises a peptide with the sequence shown in SEQ ID NO:35;

f) the light chain variable region comprises a peptide with the sequence shown in SEQ ID NO:10 and the heavy chain variable region comprises a peptide with the sequence shown in SEQ ID NO:36;

g) the light chain variable region comprises a peptide with the sequence shown in SEQ ID NO:37 and the heavy chain variable region comprises a peptide with the sequence shown in SEQ ID NO:36;

h) the light chain variable region comprises a peptide with the sequence shown in SEQ ID NO:38 and the heavy chain variable region comprises a peptide with the sequence shown in SEQ ID NO:35;

i) the light chain variable region comprises a peptide with the sequence shown in SEQ ID NO:39 and the heavy chain variable region comprises a peptide with the sequence shown in SEQ ID NO:36;

j) the light chain variable region comprises a peptide with the sequence shown in SEQ ID NO:40 and the heavy chain variable region comprises a peptide with the sequence shown in SEQ ID NO:31; or k) the light chain variable region comprises a peptide with the sequence shown in SEQ ID NO:41 and the heavy chain variable region comprises a peptide with the sequence shown in SEQ ID NO:35.

The monoclonal antibodies or antigen-binding portions thereof of the present invention can comprise a human constant region.

The antibodies or antigen-binding portions thereof disclosed herein can be used as medicaments. Thus, the present invention provides pharmaceutical compositions, comprising humanized, affinity matured monoclonal antibodies or antigen-binding portions thereof as described herein, and a pharmaceutically acceptable carrier, diluent, or excipient.

In another aspect, the present invention provides the use of a humanized, affinity matured monoclonal antibody or an antigen-binding portion thereof as described herein for the manufacture of a medicament for treatment of obesity (including morbid obesity), non-insulin dependent diabetes mellitus (NIDDM), Prader-Willi Syndrome, hyperphagia, impaired satiety, or cancer in a mammal, preferably a human.

In another aspect, the present invention provides a method of reducing food intake in, comprising administering to a patient in need thereof a therapeutically effective amount of a humanized, affinity matured monoclonal antibody or an antigen-binding portion thereof as described herein.

The present invention also provides methods of treating, preventing, or reversing conditions associated with ghrelin, including, but not limited to, obesity, morbid obesity, NIDDM, Prader-Willi Syndrome, hyperphagia, impaired satiety, and various cancers.

Further scope of the applicability of the present invention will become apparent from the detailed description provided below. However, it should be understood that the detailed description and specific examples, while indicating preferred embodiments of the present invention, are given by way of illustration only since various changes and modifications within the spirit and scope of the invention will become apparent to those skilled in the art from this detailed description.

BRIEF DESCRIPTION OF THE DRAWINGS

The above and other aspects, features, and advantages of the present invention will be better understood from the following detailed description taken in conjunction with the accompanying drawings, all of which are given by way of illustration only, and are not limitative of the present invention, wherein.

Panel A

Figure 1:
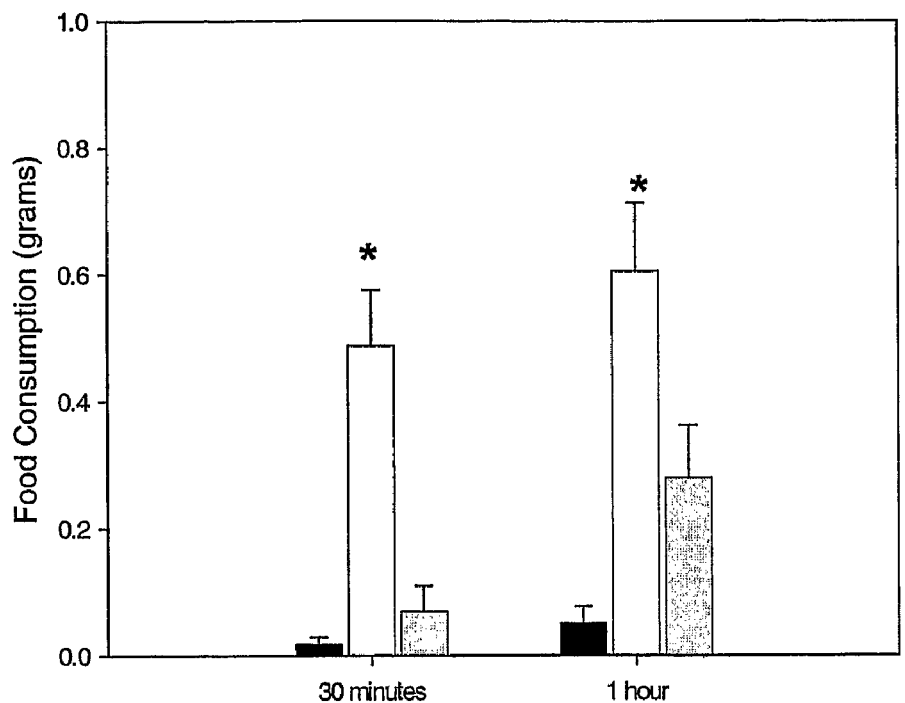
FIG. 1, panels A and B, show the effects of different C2 antibodies on food consumption at various times in an acute ghrelin rat model, as described in Example 3.
Figure 1:
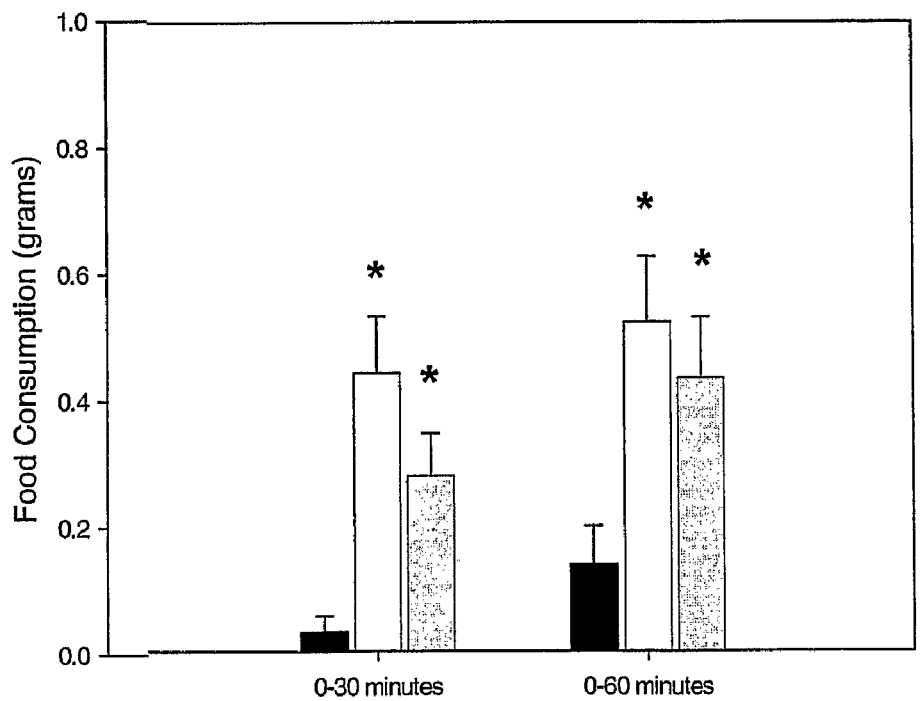

Black bar: 10 mg/kg control antibody+saline (0.1 ml/100 g s.c.) (n=24);

Open bar: 10 mg/kg control antibody+1 mg/kg human C8 acylated ghrelin (1-28) (n=24);

Gray bar: 10 mg/kg humanized, affinity matured $V_H/V_L$ (Fab C2_5a1 sequences) with rat Fc chimeric C2 anti-ghrelin antibody+1 mg/kg human C8 acylated ghrelin (n=24);

Panel B

Black bar: 10 mg/kg control antibody+saline (0.1 ml/100 g s.c.) (n=24);

Open bar: 10 mg/kg control antibody+1 mg/kg human C8 acylated ghrelin (1-28) (n=24);

Gray bar: 10 mg/kg murine $V_H/V_L$ (Fab 1111 sequences) with rat Fc chimeric C2 antibody+1 mg/kg human C8 acylated ghrelin (n=24);

DETAILED DESCRIPTION OF THE INVENTION

The following detailed description of the invention is provided to aid those skilled in the art in practicing the present invention. Even so, the following detailed description should not be construed to unduly limit the present invention as modifications and variations in the embodiments discussed herein can be made by those of ordinary skill in the art without departing from the spirit or scope of the present inventive discovery.

The contents of each of the references cited in this Detailed Description are herein incorporated by reference in their entirety.

The term "fragment" or "antigen-binding portion" of an antibody as used herein refers to one or more fragments of an antibody that retain the ability to bind to an antigen (e.g., human ghrelin). It has been shown that the antigen-binding function of an antibody can be performed by fragments of a full-length antibody. Examples of binding fragments encompassed within the term "fragment" of an antibody include (i) a Fab fragment, a monovalent fragment consisting of the VL, VH, CL and CH 1 domains; (ii) a F(ab')$_2$ fragment, a bivalent fragment comprising two Fab fragments linked by a disulfide bridge at the hinge region; (iii) an Fd fragment, consisting of the VH and CH1 domains; (iv) an Fv fragment, consisting of the VL and VH domains of a single arm of an antibody, and (v) a dAb fragment (Ward et al., *Nature* 341:544-546, 1989), which consists of a VH domain. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., *Science* 242:423-426, 1988: and Huston et al., *Proc. Natl. Acad. Sci. USA* 85:5879-5883, 1988). Such single chain antibodies are also intended to be encompassed within the term "fragment" of an antibody. Other forms of single chain antibodies, such as diabodies, are also encompassed by the present invention. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger et al., *Proc. Natl. Acad. Sci. USA* 90:6444-6448, 1993; Poljak et al., *Structure* 2:1121-1123, 1994).

Still further, an antibody or fragment thereof may be part of a larger immunoadhesion molecule, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101, 1995) and use of a cysteine residue, a marker peptide, and a C-terminal polyhistidine tag to make bivalent and biotinylated scFv molecules (Kipriyanov et al., *Mol. Immunol.* 31:1047-1058, 1994). Antibody fragments, such as Fab and F(ab')$_2$ fragments, can be prepared from whole antibodies using conventional techniques such as papain or pepsin digestion, respectively. Moreover, antibodies, antibody portions, and immunoadhesion molecules can be obtained using standard recombinant DNA techniques, as are well known in the art.

The term "humanized antibody" refers to an antibody that is composed partially or fully of amino acid sequences derived from a human antibody germline or a rearranged sequence and made by altering the sequence of an antibody having non-human complementarity determining regions (CDRs). The framework regions of the variable regions are substituted by corresponding human framework regions. As discussed herein, an antibody in the context of a humanized antibody is not limited to a full-length antibody, and can include fragments and single chain forms.

As noted above, human ghrelin was originally identified as a peptide hormone having the amino acid sequence GSSFL-SPEHQRVQQRKESKKPPAKLQPR (SEQ ID NO:1), acylated at the serine at amino acid position three ($Ser^3$) with an n-octanoyl group (referred to herein as "C8" or "C8 acylated ghrelin") (Kojima et al., Nature 402: 656-660, 1999). More recently, Hosoda et al. (Journal of Biological Chemistry 278 (1):64-69, 2003) isolated human ghrelin of the expected size, as well as several other ghrelin-derived molecules. Classified into four groups by the type of acylation observed at $Ser^3$, these peptides were found to be: non-acylated; octanoylated (C8:0); decanoylated (C10:0); and possibly decenoylated (C10:1). Furthermore, all ghrelin peptides found were either 27 or 28 amino acids in length, the former lacking the C-terminal $Arg^{28}$, and are derived from the same ghrelin precursor through two alternative pathways. The major active form of human ghrelin was identified as the 28-amino acid peptide having the sequence shown in SEQ ID NO:1, octanoylated at $Ser^3$, as was found for rat ghrelin. This peptide is identical to rat ghrelin with the exception of two residues ($Arg^{11}$-$Val^{12}$). Synthetic octanoylated and decanoylated ghrelins produced intracellular calcium increases in GHS-R-expressing cells and stimulate GH release in rats to a similar degree. Hosoda et al. found that both ghrelin and the ghrelin-derived molecules were present in plasma as well as stomach tissue. Thus, the term "acylated human ghrelin" includes the 28-amino acid peptide having the sequence shown in SEQ ID NO:1, octanoylated at $Ser^3$; octanoyl ghrelin (1-27); decanoyl ghrelin (1-28); decanoyl ghrelin (1-27); and decenoyl ghrelin (1-28). Des-acyl ghrelin (1-28) and des-acyl ghrelin (1-27) do not bind growth hormone secretagogue receptor 1a. All of these molecular forms of ghrelin were found in human plasma as well as in the stomach. Since, as shown in Table 7 below, C2 murine Fab 1111 and Mab C2 (full murine sequence, including Fc) specifically bind to human C10 ghrelin (1-28), and since the epitope for this Fab and this Mab is between amino acids 1 and 8 of C8 acylated human ghrelin, the humanized, affinity-matured monoclonal antibodies and antigen-binding portions thereof of the present invention presumably bind decanoyl ghrelin (1-27) and decenoyl ghrelin (1-28) as well. It is further presumed that the monoclonal antibodies and antigen-binding portions thereof of the present invention specifically bind to full-length (1-28) and truncated forms of acylated human ghrelins (whether containing a $Ser^3$ n-octanoyl, n-decanoyl, or n-decenoyl group, or other fatty acid) that retain the epitope contained within amino acids 1-8 at the N-terminus.

Affinity maturation refers to the process by which the affinity of an antibody, or antigen-binding portion thereof, to its antigen is increased. This results in a lowering of the $K_d$ of the molecule for that antigen. Methods for affinity maturation are well known in the art.

The term "$K_d$", as used herein, is intended to refer to the dissociation constant of a particular antibody-antigen interaction. It is calculated by the formula:

$$K_d = k_{off}/k_{on} \text{(measured in } M\text{)}$$

The term "$k_{on}$" as used herein is intended to refer to the association rate constant, or specific reaction rate, of the forward, or complex-forming, reaction, measured in units: $M^{-1} sec^{-1}$. The term "$k_{off}$", as used herein, is intended to refer to the dissociation rate constant, or specific reaction rate, for dissociation of an antibody from the antibody/antigen complex, measured in units: $sec^{-1}$.

Antibodies, or antigen-binding portions thereof, are defined to "specifically bind" if they bind to acylated human ghrelin with a $K_d$ of about $10^{-8}$ M or less, more preferably about $10^{-9}$ M or less, and most preferably about $5 \times 10^{-10}$ M or less, i.e., in the range of from about $10^{-8}$ M or less to about $5 \times 10^{-10}$ M or less. Even more preferable antibodies or antigen-binding portions thereof exhibit $K_d$s for acylated human ghrelin of about $10^{-11}$ M or less, more preferably about $250 \times 10^{-12}$ M or less. Such antibodies or antigen-binding portions thereof can exhibit $K_d$s for acylated human ghrelin in the range of from about 100 pM to about 1 pM, more preferably from about 50 pM to about 1 pM, more preferably from about 25 pM to about 1 pM, and even more preferably from about 15 pM to about 1 pM. Thus, the most preferred antibodies or antigen-binding portions thereof of the present invention exhibit $K_d$s for acylated human ghrelin in the range of from about $10^{-11}$ M to about 1 pM. As shown by the data in Examples 1 and 2, below, humanized, affinity matured Fabs and Mabs of the present invention exhibit $K_d$s for C8 human ghrelin in the range of from about 1 pM to about 25 pM, and about 1 pM to about 15 pM, respectively.

The antibodies and antigen-binding portions thereof of the present invention include humanized antibodies. An important aspect of humanizing antibodies from another species is to reduce the possibility that the antibody causes an immune response when injected into a human patient as a therapeutic. The more sequences that are employed in a humanized antibody resemble those of human antibodies, the lower the risk of immunogenicity. In addition, the injected humanized antibodies generally have a longer half-life in the circulation than injected non-human antibodies. Furthermore, if effector function is desired, because the effector portion is human, it may interact better with the other parts of the human immune system.

The preferred human framework amino acid sequence for the light chain variable region of the antibodies of the present invention includes the following sequence, which for illustrative purposes is represented with the CDRs of Fab 1a1 disclosed herein (underlined sequences) inserted:

```
                                          (SEQ ID NO:10)
DIVMTQSPDSLAVSLGERATINCRASKSVSTLGYSYMHWYQQKPGQPPKL

LIYFASNLESGVPDRFSGSGSGTDFTLTISSLQAEDVAVYYCQHSVEEPY

TFGQGTKLEIK
```

The preferred human framework amino acid sequence for the heavy chain variable region of the antibodies of the present invention includes the following sequence, which for illustrative purposes is represented with the CDRs of Fab 1a1 (underlined sequences) inserted:

(SEQ ID NO:11)
QVQLVQSGAEVKKPGASVKVSCKAT<u>GYIFTGYWIE</u>WVRQAPGQGLEWMG<u>D

LLPGSGTPNYNEKFKG</u>RVTMTTDTSTSTAYMELRSLRSDDTAVYYCAR<u>YP

QFRPRTERIAY</u>WGQGTLVTVSS

The antibodies of the present invention, or antigen-binding fragments thereof, contain light chain and heavy chain CDRs with amino acid sequences selected from the group consisting of: SEQ ID NO:4 for CDR L1; SEQ ID NO:5 for CDR L2; SEQ ID NO:6 for CDR L3; SEQ ID NO:7 for CDR H1; SEQ ID NO:8 for CDR H2; and SEQ ID NO:9 for CDR H3. See Tables 1 and 2.

Preferred embodiments include light chain and heavy chain CDRs with amino acid sequences selected from the group consisting of: SEQ ID NOS: 12, 13, 14, 15, and 16 for CDR L1; SEQ ID NOS: 17 and 18 for CDR L2; SEQ ID NOS: 19 and 20 for CDR L3; SEQ ID NO:7 for CDR H1; SEQ ID NOS: 21, 22, 23, and 24 for CDR H2; and SEQ ID NOS: 25, 26, 27 and 28 for CDR H3. See Tables 1 and 2.

TABLE 1

CDR Sequences-Light Chain Variable Region (LCVR)

| FAb | CDR1 | CDR2 | CDR3 |
|---|---|---|---|
| 1a1 | RASKSVSTLGYSYMH (SEQ ID NO:12) | FASNLES (SEQ ID NO:17) | QHSVEEPYT (SEQ ID NO:19) |
| 2a1 | RASKSVSTLGYSYMH (SEQ ID NO:12) | FASNLES (SEQ ID NO:17) | QHSVEEPYT (SEQ ID NO:19) |
| 3a1 | RASKSVSTGGYSYMH (SEQ ID NO:13) | FASNLES (SEQ ID NO:17) | QHSIEEPYT (SEQ ID NO:20) |
| 4a1 | RASKSVSLSDYSYMH (SEQ ID NO:14) | FASNLES (SEQ ID NO:17) | QHSIEEPYT (SEQ ID NO:20) |
| 5a1 | RASKSVSLSGYSYMH (SEQ ID NO:15) | FASNLES (SEQ ID NO:17) | QHSIEEPYT (SEQ ID NO:20) |
| 6a1 | RASKSVSTLGYSYMH (SEQ ID NO:12) | FASNLES (SEQ ID NO:17) | QHSVEEPYT (SEQ ID NO:19) |
| 7a1 | RASKSVSLLGYSYMH (SEQ ID NO:16) | FASNLES (SEQ ID NO:17) | QHSVEEPYT (SEQ ID NO:19) |
| 7b2 | RASKSVSLLGYSYMH (SEQ ID NO:16) | FASNLES (SEQ ID NO:17) | QHSIEEPYT (SEQ ID NO:20) |
| 8a1 | RASKSVSLSGYSYMH (SEQ ID NO:15) | FASNLES (SEQ ID NO:17) | QHSVEEPYT (SEQ ID NO:19) |
| 9a1 | RASKSVSTLGYSYMH (SEQ ID NO:12) | FASNLES (SEQ ID NO:17) | QHSIEEPYT (SEQ ID NO:20) |
| 10a1 | RASKSVSTGGYSYMH (SEQ ID NO:13) | LASNLES (SEQ ID NO:18) | QHSVEEPYT (SEQ ID NO:19) |
| Consensus | RASKSVSX$_{27D}$X$_{28}$X$_{29}$YSYMH (SEQ ID NO:4) | X$_{50}$ASNLES (SEQ ID NO:5) | QHSX$_{92}$EEPYT (SEQ ID NO:6) |

X$_{27D}$ is T or L; X$_{28}$ is L, G, or S; and X$_{29}$ is G or D
X$_{50}$ is F or L
X$_{92}$ is V or I

TABLE 2

CDR Sequences-Heavy Chain Variable Region (HCVR)

| Fab | CDR1 | CDR2 | CDR3 |
|---|---|---|---|
| 1a1 | GYIFTGYWIE (SEQ ID NO:7) | DLLPGSGTPNYNEKFKG (SEQ ID NO:21) | YPQFRPRTEPIAY (SEQ ID NO:25) |
| 2a1 | GYIFTGYWIE (SEQ ID NO:7) | DILPGSGTPNYNEKFKG (SEQ ID NO:22) | YPIFRLRTERIAE (SEQ ID NO:26) |
| 3a1 | GYIFTGYWIE (SEQ ID NO:7) | DLLPGSGSPNYNEKFKG (SEQ ID NO:23) | YPIFRLRTERIAE (SEQ ID NO:26) |
| 4a1 | GYIFTGYWIE (SEQ ID NO:7) | DILPGSGTPNYNEKFKG (SEQ ID NO:22) | YPQFRLRTERIAE (SEQ ID NO:27) |
| 5a1 | GYIFTGYWIE (SEQ ID NO:7) | DILPGSGSPNYNEKFKG (SEQ ID NO:24) | YPIFRLRTERIAE (SEQ ID NO:26) |
| 6a1 | GYIFTGYWIE (SEQ ID NO:7) | DILPGSGSPNYNEKFKG (SEQ ID NO:24) | YPIFRPRTERIAY (SEQ ID NO:28) |
| 7a1 | GYIFTGYWIE (SEQ ID NO:7) | DILPGSGSPNYNEKFKG (SEQ ID NO:24) | YPIFRPRTERIAY (SEQ ID NO:28) |
| 7b2 | GYIFTGYWIE (SEQ ID NO:7) | DILPGSGSPNYNEKFKG (SEQ ID NO:24) | YPIFRLRTERIAE (SEQ ID NO:26) |

TABLE 2-continued

CDR Sequences-Heavy Chain Variable Region (HCVR)

| Fab | CDR1 | CDR2 | CDR3 |
|---|---|---|---|
| 8a1 | GYIFTGYWIE (SEQ ID NO:7) | DILPGSGSPNYNEKFKG (SEQ ID NO:24) | YPIFRPRTERIAY (SEQ ID NO:28) |
| 9a1 | GYIFTGYWIE (SEQ ID NO:7) | DLLPGSGSPNYNEKFKG (SEQ ID NO:23) | YPIFRLRTERIAE (SEQ ID NO:26) |
| 10a1 | GYIFTGYWIE (SEQ ID NO:7) | DILPGSGSPNYNEKFKG (SEQ ID NO:24) | YPIFRLRTERIAE (SEQ ID NO:26) |
| Consensus | GYIFTGYWIE (SEQ ID NO:7) | $DX_{51}LPGSGX_{56}PNYNEKFKG$ (SEQ ID NO:8) | $YPX_{97}FRX_{100}RTERIAX_{102}$ (SEQ ID NO:9) |

Where:
$X_{51}$ is L or I; $X_{56}$ is T or S.
$X_{97}$ is I or Q; $X_{100}$ is P or L; and $X_{102}$ is Y or E.

Even more preferred embodiments include antibodies or antigen-binding fragments thereof with the following sequences:

1) SEQ ID NO:13 for CDR L1, SEQ ID NO:17 for CDR L2, SEQ ID NO:20 for CDR L3, SEQ ID NO:7 for CDR H1, SEQ ID NO:23 for CDR H2, and SEQ ID NO:26 for CDR H3.
2) SEQ ID NO:14 for CDR L1, SEQ ID NO:17 for CDR L2, SEQ ID NO:20 for CDR L3, SEQ ID NO:7 for CDR H1, SEQ ID NO:22 for CDR H2, and SEQ ID NO:27 for CDR H3.
3) SEQ ID NO:15 for CDR L1, SEQ ID NO:17 for CDR L2, SEQ ID NO:20 for CDR L3, SEQ ID NO:7 for CDR H1, SEQ ID NO:24 for CDR H2, and SEQ ID NO:26 for CDR H3.
4) SEQ ID NO:12 for CDR L1, SEQ ID NO:17 for CDR L2, SEQ ID NO:19 for CDR L3, SEQ ID NO:7 for CDR H1, SEQ ID NO:24 for CDR H2, and SEQ ID NO:28 for CDR H3.
5) SEQ ID NO:16 for CDR L1, SEQ ID NO:17 for CDR L2, SEQ ID NO:19 for CDR L3, SEQ ID NO:7 for CDR H1, SEQ ID NO:24 for CDR H2, and SEQ ID NO:28 for CDR H3.
6) SEQ ID NO:16 for CDR L1, SEQ ID NO:17 for CDR L2, SEQ ID NO:20 for CDR L3, SEQ ID NO:7 for CDR H1, SEQ ID NO:24 for CDR H2, and SEQ ID NO:26 for CDR H3.
7) SEQ ID NO:15 for CDR L1, SEQ ID NO:17 for CDR L2, SEQ ID NO:19 for CDR L3, SEQ ID NO:7 for CDR H1, SEQ ID NO:24 for CDR H2, and SEQ ID NO:28 for CDR H3.
8) SEQ ID NO:12 for CDR L1, SEQ ID NO:17 for CDR L2, SEQ ID NO:20 for CDR L3, SEQ ID NO:7 for CDR H1, SEQ ID NO:23 for CDR H2, and SEQ ID NO:26 for CDR H3.
9) SEQ ID NO:12 for CDR L1, SEQ ID NO:17 for CDR L2, SEQ ID NO:19 for CDR L3, SEQ ID NO:7 for CDR H1, SEQ ID NO:21 for CDR H2, and SEQ ID NO:25 for CDR H3.
10) SEQ ID NO:12 for CDR L1, SEQ ID NO:17 for CDR L2, SEQ ID NO:19 for CDR L3, SEQ ID NO:7 for CDR H1, SEQ ID NO:22 for CDR H2, and SEQ ID NO:26 for CDR H3.
11) SEQ ID NO:13 for CDR L1, SEQ ID NO:18 for CDR L2, SEQ ID NO:19 for CDR L3, SEQ ID NO:7 for CDR H1, SEQ ID NO:24 for CDR H2, and SEQ ID NO:26 for CDR H3.

Most preferred embodiments include antibodies or antigen-binding fragments thereof with the following:

1) A LCVR with the sequence as shown in SEQ ID NO:10, and a HCVR with the sequence as shown in SEQ ID NO:11.
2) A LCVR with the sequence as shown in SEQ ID NO:10, and a HCVR with the sequence as shown in SEQ ID NO:29.
3) A LCVR with the sequence as shown in SEQ ID NO:30, and a HCVR with the sequence as shown in SEQ ID NO:31.
4) A LCVR with the sequence as shown in SEQ ID NO:32, and a HCVR with the sequence as shown in SEQ ID NO:33.
5) A LCVR with the sequence as shown in SEQ ID NO:34, and a HCVR with the sequence as shown in SEQ ID NO:35.
6) A LCVR with the sequence as shown in SEQ ID NO:10, and a HCVR with the sequence as shown in SEQ ID NO:36.
7) A LCVR with the sequence as shown in SEQ ID NO:37, and a HCVR with the sequence as shown in SEQ ID NO:36.
8) A LCVR with the sequence as shown in SEQ ID NO:38, and a HCVR with the sequence as shown in SEQ ID NO:35.
9) A LCVR with the sequence as shown in SEQ ID NO:39, and a HCVR with the sequence as shown in SEQ ID NO:36.
10) A LCVR with the sequence as shown in SEQ ID NO:40, and a HCVR with the sequence as shown in SEQ ID NO:31.
11) A LCVR with the sequence as shown in SEQ ID NO:41, and a HCVR with the sequence as shown in SEQ ID NO:35.

The CDRs described herein can be used to make full-length antibodies as well as functional fragments and analogs or other proteins, which incorporate the CDRs in an active structural conformation, such that the protein employing the CDRs binds acylated ghrelin.

The Fabs of the present invention shown in Tables 3 and 4 differ from each other by sequence changes in at least 1 CDR, and in up to as many as 6 CDRs. One CDR L1 may be substituted for another CDR L1, one CDR L2 substituted for another CDR L2, and so forth.

TABLE 3

FAb Light Chain Variable Region Alignment

```
Fab
                                                CDR1
  1a1   DIVMTQSPDS LAVSLGERAT INCRASKSVS TLGYSYMHWY
  2a1   DIVMTQSPDS LAVSLGERAT INCRASKSVS TLGYSYNHWY
  3a1   DIVMTQSPDS LAVSLGERAT INCRASKSVS TGGYSYMHWY
  4a1   DIVMTQSPDS LAVSLGERAT INCRASKSVS LSDYSYMHWY
  5a1   DIVMTQSPDS LAVSLGERAT INCRASKSVS LSGYSYMHWY
  6a1   DIVMTQSPDS LAVSLGERAT INCRASKSVS TLGYSYMMWY
  7a1   DIVMTQSPDS LAVSLGERAT INCRASKSVS LLGYSYMHWY
  7b2   DIVMTQSPDS LAVSLGERAT INCRASKSVS LLGYSYMHWY
  8a1   DIVMTQSPDS LAVSLGERAT INCRASKSVS LSGYSYMHWY
  9a1   DIVMTQSPDS LAVSLGERAT INCRASKSVS TLGYSYMHWY
 10a1   DIVMTQSPDS LAVSLGERAT INCRASKSVS TGGYSYMHWY

CDR2
  1a1   QQKPGQPPKL LIYFASNLES GVPDRFSGSG SGTDFTLTIS
  2a1   QQKPGQPPKL LIYFASNLES GVPDRFSGSG SGTDFTLTIS
  3a1   QQKPGQPPKL LIYFASNLES GVPDRFSGSG SGTDFTLTIS
  4a1   QQKPGQPPKL LIYFASNLES GVPDRFSGSG SGTDFTLTIS
  5a1   QQKPGQPPKL LIYFASNLES GVPDRFSGSG SGTDFTLTIS
  6a1   QQKPGQPPKL LIYFASNLES GVPDRFSGSG SGTDFTLTIS
  7a1   QQKPGQPPKL LIYFASNLES GVPDRFSGSG SGTDFTLTIS
  7b2   QQKPGQPPKL LIYFASNLES GVPDRFSGSG SGTDFTLTIS
  8a1   QQKPGQPPKL LIYFASNLES GVPDRFSGSG SGTDFTLTIS
  9a1   QQKPGQPPKL LIYFASNLES GVPDRFSGSG SGTDFTLTIS
 10a1   QQKPGQPPKL LIYLASNLES GVPDRFSGSG SGTDFTLTIS

CDR3
  1a1   SLQAEDVAVY YCQHSVEEPY TFGQGTKLEI K   (SEQ ID NO:10)
  2a1   SLQAEDVAVY YCQHSVEEPY TFGQGTKLEI K   (SEQ ID NO:10)
  3a1   SLQAEDVAVY YCQHSIEEPY TFGQGTKLEI K   (SEQ ID NO:30)
  4a1   SLQAEDVAVY YCQHSIEEPY TFGQGTKLEI K   (SEQ ID NO:32)
  5a1   SLQAEDVAVY YCQHSIEEPY TFGQGTKLEI K   (SEQ ID NO:34)
  6a1   SLQAEDVAVY YCQHSVEEPY TFGQGTKLEI K   (SEQ ID NO:10)
  7a1   SLQAEDVAVY YCQHSVEEPY TFGQGTKLEI K   (SEQ ID NO:37)
  7b2   SLQAEDVAVY YCQHSIEEPY TFGQGTKLEI K   (SEQ ID NO:38)
  8a1   SLQAEDVAVY YCQHSVEEPY TFGQGTKLEI K   (SEQ ID NO:39)
  9a1   SLQAEDVAVY YCQHSIEEPY TFGQGTKLEI K   (SEQ ID NO:40)
 10a1   SLQAEDVAVY YCQHSVEEPY TFGQGTKLEI K   (SEQ ID NO:41)
```

TABLE 4

Fab Heavy Chain Variable Region Alignment

```
Fab
                                        CDR1
  1a1   QVQLVQSGAE VKKPGASVKV SCKATGYIFT GYWIEWVRQA
  2a1   QVQLVQSGAE VKKPGASVKV SCKATGYIFT GYWIEWVRQA
  3a1   QVQLVQSGAE VKKPGASVKV SCKATGYIFT GYWIEWVRQA
  4a1   QVQLVQSGAE VKKPGASVKV SCKATGYIFT GYWIEWVRQA
  5a1   QVQLVQSGAE VKKPGASVKV SCKATGYIFT GYWIEWVRQA
  6a1   QVQLVQSGAE VKKPGASVKV SCKATGYIFT GYWIEWVRQA
  7a1   QVQLVQSGAE VKKPGASVKV SCKATGYIFT GYWIEWVRQA
  7b2   QVQLVQSGAE VKKPGASVKV SCKATGYIFT GYWIEWVRQA
  8a1   QVQLVQSGAE VKKPGASVKV SCKATGYIFT GYWIEWVRQA
  9a1   QVQLVQSGAE VKKPGASVKV SCKATGYIFT GYWIEWVRQA
 10a1   QVQLVQSGAE VKKPGASVKV SCKATGYIFT GYWIEWVRQA

CDR2
  1a1   PGQGLEWMGD LLPGSGTPNY NEKFKGRVTM TTDTSTSTAY
  2a1   PGQGLEWMGD ILPGSGTPNY NEKFKGRVTM TTDTSTSTAY
  3a1   PGQGLEWMGD LLPGSGSPNY NEKFKGRVTM TTDTSTSTAY
  4a1   PGQGLEWMGD ILPGSGTPNY NEKFKGRVTM TTDTSTSTAY
  5a1   PGQGLEWMGD ILPGSGSPNY NEKFKGRVTM TTDTSTSTAY
  6a1   PGQGLEWMGD LLPGSGSPNY NEKFKGRVTM TTDTSTSTAY
  7a1   PGQGLEWMGD ILPGSGSPNY NEKFKGRVTM TTDTSTSTAY
  7b2   PGQGLEWMGD ILPGSGSPNY NEKFKGRVTM TTDTSTSTAY
  8a1   PGQGLEWMGD ILPGSGSPNY NEKFKGRVTM TTDTSTSTAY
  9a1   PGQGLEWMGD LLPGSGSPNY NEKFKGRVTM TTDTSTSTAY
 10a1   PGQGLEWMGD ILPGSGSPNY NEKFKGRVTM TTDTSTSTAY
```

TABLE 4-continued

Fab Heavy Chain Variable Region Alignment

Fab

```
                                CDR3
1a1   MELRSLRSDD TAVYYCARYP QFRPRTERIA YWGQGTLVTVSS (SEQ ID NO:11)
2a1   MELRSLRSDD TAVYYCARYP IFRLRTERIA EWGQGTLVTVSS (SEQ ID NO:29)
3a1   MELRSLRSDD TAVYYCARYP IFRLRTERIA EWGQGTLVTVSS (SEQ ID NO:31)
4a1   MELRSLRSDD TAVYYCARYP QFRLRTERIA EWGQGTLVTVSS (SEQ ID NO:33)
5a1   MELRSLRSDD TAVYYCARYP IFRLRTERIA EWGQGTLVTVSS (SEQ ID NO:35)
6a1   MELRSLRSDD TAVYYCARYP IFRPRTERIA YWGQGTLVTVSS (SEQ ID NO:36)
7a1   MELRSLRSDD TAVYYCARYP IFRPRTERIA YWGQGTLVTVSS (SEQ ID NO:36)
7b2   MELRSLRSDD TAVYYCARYP IFRLRTERIA EWGQGTLVTVSS (SEQ ID NO:35)
8a1   MELRSLRSDD TAVYYCARYP IFRPRTERIA YWGQGTLVTVSS (SEQ ID NO:36)
9a1   MELRSLRSDD TAVYYCARYP IFRLRTERIA EWGQGTLVTVSS (SEQ ID NO:31)
10a1  MELRSLRSDD TAVYYCARYP IFRLRTERIA EWGQGTLVTVSS (SEQ ID NO:35)
```

The affinity of a given antibody for acylated ghrelin is one of several properties that is likely to contribute to its utility for a particular application of the antibody. In one embodiment, antibodies of the present invention will have an affinity for acylated human ghrelin equal to or, more preferably, greater than that of C2 murine Fab 1111, as determined by $K_d$. Affinity can be improved by increasing the $k_{on}$ or decreasing the $k_{off}$. Several exemplary antibodies or Fabs listed in Tables 3 and 4 have improved affinity for acylated ghrelin, based on determination of $K_d$ or $k_{on}$, as disclosed in Examples 1 and 2, below.

The antibodies or antigen-binding portions thereof of the present invention can be present in a relatively pure or isolated form, as well as in a supernatant drawn from cells grown in wells or on plates. The antibodies or antigen-binding portions thereof of the present invention can also be present in the form of a composition, comprising an antibody or antigen-binding portion thereof of the invention and a pharmacologically or pharmaceutically acceptable carrier, diluent, or excipient, in which the molecule is suspended. The antibodies or antigen-binding portions thereof of the present invention can be present in such a composition at a concentration, or in an amount, sufficient to be of therapeutic or pharmacological value in treating or preventing obesity and related diseases, and various cancers. The antibodies or antigen-binding portions thereof can also be present in a composition in a more dilute form.

An antibody or antigen-binding portion thereof of the present invention can be incorporated into pharmaceutical compositions suitable for administration to a subject. The compounds of the invention can be administered alone, or in combination with a pharmaceutically acceptable carrier, diluent, and/or excipients, in single or multiple doses. The pharmaceutical compositions for administration are designed to be appropriate for the selected mode of administration, and pharmaceutically acceptable diluents, carrier, and/or excipients such as dispersing agents, buffers, surfactants, preservatives, solubilizing agents, isotonicity agents, stabilizing agents, and the like are used as appropriate. Such compositions are designed in accordance with conventional techniques as described in, e.g., Remington, *The Science and Practice of Pharmacy*, 19th Edition, Gennaro, Ed., Mack Publishing Co., Easton, Pa., 1995, which provides a compendium of formulation techniques as are generally known to practitioners.

In another embodiment, the present invention is also directed to cell lines that produce an anti-ghrelin monoclonal antibody or antigen-binding portion thereof of the invention. Creation and isolation of such cell lines can be accomplished using routine screening techniques known in the art.

An antibody or antigen-binding portion thereof of the present invention can also be prepared by recombinant expression of immunoglobulin light and heavy chain genes in a host cell. Standard recombinant DNA methodologies are used to obtain antibody heavy and light chain genes, incorporate these genes into recombinant expression vectors, and introduce these vectors into host cells. Such standard recombinant DNA technologies are described, for example, in Sambrook, Fritsch, and Maniatis (Eds.), *Molecular Cloning; A Laboratory Manual*, Second Edition, Cold Spring Harbor, N.Y., (1989); Ausubel, et al (Eds.) *Current Protocols in Molecular Biology*, Greene Publishing Associates, (1989); and in U.S. Pat. No. 4,816,397.

An isolated DNA encoding a HCVR region can be converted to a full-length heavy chain gene by operably linking the HCVR-encoding DNA to another DNA molecule encoding heavy chain constant regions (CH1, CH2, and CH3). The sequences of human heavy chain constant region genes are known in the art. See, e.g., Kabat et al., *Sequences of Proteins of Immunological Interest*, Fifth Edition, U.S. Department of Health and Human Services, NIH Publication No. 91-3242 (1991). DNA fragments encompassing these regions can be obtained by standard PCR amplification. The heavy chain constant region can be an IgG (further divided into isotypes IgG1, IgG2, IgG3, and IgG4), IgA, IgE, IgM, or IgD constant region, and any allotypic variant thereof as described in Kabat (supra), but most preferably is an IgG4 or an IgG1 constant region. Alternatively, the antigen binding portion can be a Fab fragment, a F(ab')$_2$ fragment, or a single chain Fv fragment (scFv). For a Fab fragment heavy chain gene, the HCVR-encoding DNA can be operably linked to another DNA molecule encoding only a heavy chain CH1 constant region.

An isolated DNA encoding an LCVR region can be converted to a full-length light chain gene (as well as a Fab light chain gene) by operably linking the LCVR-encoding DNA to another DNA molecule encoding a light chain constant region, CL. The sequences of human light chain constant region genes are known in the art. See, e.g., Kabat, supra.

DNA fragments encompassing these regions can be obtained by standard PCR amplification. The light chain constant region can be a kappa or lambda constant region.

In a preferred system for recombinant expression of an antibody or antigen-binding portion thereof of the invention, a recombinant expression vector encoding both the antibody heavy chain and the antibody light chain is introduced into DHFR-CHO cells by calcium phosphate-mediated transfection. Within the recombinant expression vector, the antibody heavy and light chain genes are each operably linked to enhancer/promoter regulatory elements (e.g., derived from SV40, CMV, adenovirus, and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains, and intact antibody or antigen-binding portion thereof is recovered from the culture medium. Standard molecular biology techniques are used to prepare the recombinant expression vector, transfect the host cells, select for transformants, culture the host cells, and recover the antibody or or antigen-binding portion thereof from the culture medium. Antibodies, or antigen-binding portions thereof, of the invention can be expressed in an animal (e.g., a goat) that is transgenic for an antibody of the invention. Plant cells can also be modified to create transgenic plants that express the antibody, or an antigen-binding portion thereof, of the invention.

In view of the foregoing, another embodiment of the invention pertains to nucleic acids, vectors, and host cell compositions that can be used for recombinant expression of the antibodies and antigen-binding portions thereof of the present invention. Preferably, the invention provides isolated nucleic acids that encode an anti-ghrelin monoclonal antibody or antigen-binding portion thereof comprising one or more CDRs with a sequence as shown in SEQ ID NOS: 4, 5, 6, 7, 8, or 9. Preferably, the invention provides isolated nucleic acids that encode the light chain variable region and heavy chain variable region of an anti-ghrelin monoclonal antibody or antigen-binding portion thereof comprising a LCVR amino acid sequence as shown in SEQ ID NO:42 and a HCVR amino acid sequence as shown in SEQ ID NO:43:

```
Light Chain Variable Region Consensus Sequence (SEQ ID NO:42)
1                                     CDR1            40
DIVMTQSPDS LAVSLGERAT INCRASKSVS X27DX28X29YSYMHWY 41                   CDR2                              80
QQKPGQPPKL LIYX50ASNLES GVPDRFSGSG SGTDFTLTIS

81               CDR3             111
SLQAEDVAVY YCQHSX92EEPY TFGQGTKLEI K

Wherein:

X27D = T or L;

X28 = L, G or S; and X29 = G or D

X50 = F or L

X92 = V or I

Heavy Chain Variable Region Consensus Sequence (SEQ ID NO:43)
1                                     CDR1            40
QVQLVQSGAE VKKPGASVKV SCKATGYIFT GYWIEWVRQA 41                   CDR2                              80
PGQGLEWMGD X51LPGSGX56PNY NEKFKGRVTM TTDTSTSTAY 81                        CDR3                        120
MELRSLRSDD TAVYYCARYP X97FRX100RTERIA X102WGQGTLVTV

122
SS

Wherein:

X51 = L or I; X56 = T or S

X97 = I or Q; X100 = P or L; and X102 = Y or E
```

The present invention also provides recombinant expression vectors encoding both an antibody heavy chain and/or an antibody light chain. For example, in one embodiment, the invention provides a recombinant expression vector encoding:

a) an antibody heavy chain having a variable region comprising at least one peptide with an amino acid sequence selected from the group consisting of SEQ ID NOS: 7 and 21-28; and further comprising, b) an antibody light chain having a variable region comprising at least one peptide with an amino acid sequence selected from the group consisting of SEQ ID NOS: 12-20.

The invention also provides host cells into which one or more of the recombinant expression vectors of the invention have been introduced. Preferably, the host cell is a mammalian host cell, more preferably the host cell is a CHO cell, an NS0 cell, a COS cell, or a yeast cell. Still further, the invention provides a method of synthesizing a recombinant human antibody or antigen-binding portion thereof of the invention by culturing a host cell of the invention in a suitable culture medium until a recombinant humanized antibody or antigen-binding portion thereof is synthesized. The method can further comprise isolating the recombinant human antibody or antigen-binding portion thereof from the culture medium.

Once expressed, the intact antibodies, their dimers, individual light and heavy chains, or other immunoglobulin forms of the present invention can be purified according to standard procedures of the art, including ammonium sulfate precipitation, ion exchange, affinity, reverse phase, hydrophobic interaction column chromatography, gel electrophoresis, and the like.

Humanized Antibodies

Humanized antibodies have at least three potential advantages over non-human and chimeric antibodies for use in human therapy:

1) Because the effector portion is human, they may interact better with the other parts of the human immune system (e.g., destroy the target cells more efficiently by complement-dependent cytotoxicity or antibody-dependent cellular cytotoxicity);

2) The human immune system should not recognize the framework or constant region of the humanized antibody as foreign, and therefore the antibody response against such an injected antibody should be less than that against a totally foreign, non-human antibody or a partially foreign chimeric antibody;

3) Injected non-human antibodies have been reported to have a half-life in the human circulation much shorter than the half-life of human antibodies. Injected humanized antibodies will have a half-life essentially identical to naturally occurring human antibodies, allowing smaller and less frequent doses to be given.

Antibody humanization traditionally involves the direct transfer, or grafting, of murine CDRs into a human framework, followed by the reinsertion of critical murine residues in the framework regions. See Queen et al., *Proc. Natl. Acad. Sci. USA* 88:2869, 1991; U.S. Pat. Nos. 5,693,761; 4,816,397; 5,225,539; computer programs ABMOD and ENCAD as described in Levitt, M., *J. Mol. Biol.* 168:595-620, 1983.

Since traditional humanization procedures usually result in a loss of binding activity, a better approach to humanization is the combination of fully human frameworks with synthetic CDRs to yield high affinity antibodies that are devoid of any potentially immunogenic murine residues in the framework regions. Fully human, functional frameworks for both chains are selected from among commonly occurring germline genes in order to maximize the occurrence of tolerance in the relevant patient populations. Libraries of synthetic CDR variants closely related to those of the parent molecule are then inserted into the selected frameworks and a functional assay is employed to identify amino acid changes in the CDRs that accommodate the new framework and simultaneously improve affinity.

The present invention further embraces variants and their equivalents that are substantially homologous to the humanized antibodies and antibody fragments disclosed herein that maintain the affinity of the parent molecule. These are contemplated to contain conservative amino acid substitution mutations that do not affect affinity.

Uses

Ghrelin plays a role in the pathophysiology of obesity and a number of related disorders or diseases, and has been implicated in a number of cancers. Ghrelin is the first circulating hormone shown to stimulate feeding in humans following systemic administration. One study demonstrated that obese subjects do not demonstrate the decline in plasma ghrelin levels seen after a meal in lean subjects, and may therefore lead to increased food consumption (English et al., *J. Clin. End. & Metabolism,* 87:2984-2987, 2002). Therefore, a pharmaceutical composition comprising an anti-ghrelin monoclonal antibody or antigen-binding portion thereof of the present invention can be used to treat or prevent obesity and/or obesity-related disorders such as NIDDM, Prader-Willi syndrome, impaired satiety, and hyperphagia, as well as certain cancers.

Obesity, also called corpulence or fatness, is the excessive accumulation of body fat, usually caused by the consumption of more calories than the body uses. The excess calories are then stored as fat, or adipose tissue. To be overweight, if moderate, is not necessarily to be obese, e.g., in muscular individuals. In general, however, a body weight of a subject that is 20 percent or more over the optimum tends to be associated with obesity. Alternatively, obesity may be defined in terms of Body Mass Index (BMI). Human BMI is defined as the body weight of a human in kilograms divided by the square of the height of that individual in meters. Typically, persons with a BMI of between 25 and 29 are considered overweight and a BMI of 29 or greater is considered obese. This may vary in some persons due to differences in gender or body frame. However, a BMI of 25 or greater typically defines the point where the risk of disease increases due to excess weight. Assays for measuring energy expenditure, body composition, and weight loss in animals that would be useful for determining effect of an antibody of the invention on an obese subject are known in the art, see e.g., International Patent Publication Number WO 01/87335.

Hunger is a desire for food, and is normal. Hyperphagia and impaired satiety are defined as excessive ingestion of food beyond that needed for basic energy requirements. Ingestion may occupy unusual amounts of time. Eating may be obligatory and disrupt normal activity, and can be symptomatic of various disorders. Hyperphagic or impaired satiety conditions may occur in association with central nervous system (CNS) disorders including gangliocytoma of the third ventricle, hypothalmic astrocytoma, Kleine-Levin Syndrome, Froehlich's Syndrome, Parkinson's Disease, genetic disorders including Prader-Willi Syndrome (deletion on the long arm of chromosome 15), psychiatric disorders including anxiety, major depressive disorder, depressive phase of bipolar disorder, seasonal affective disorder, and schizophrenia.

Psychotropic medications, including delta-9 tetrahydrocannabinol, antidepressants, and neuroleptics may induce hyperphagia. Sleep disorders including sleep apnea are also associated with hyperphagia.

Type II diabetes mellitus, also called non-insulin dependent diabetes mellitus (NIDDM), is present in subjects whose insulin their body is still capable of producing is not physiologically effective. An individual can be predisposed to NIDDM by both genetic and environmental factors. Heredity, obesity, and increased age play a major role in the onset of NIDDM. Risk factors include prolonged stress, sedentary lifestyle, and certain medications affecting hormonal processes in the body. Eighty percent or more of the people with NIDDM are obese, indicating obesity to be a predominant link to the development of NIDDM.

The use of an anti-ghrelin monoclonal antibody or antigen-binding portion thereof of the present invention for the treatment of at least one of the aforementioned disorders in which ghrelin activity is detrimental is also contemplated herein. Additionally, the use of an anti-ghrelin monoclonal antibody or antigen-binding portion thereof of the present invention for use in the manufacture of a medicament for the treatment of at least one of the aforementioned disorders in which ghrelin activity is detrimental is contemplated.

A pharmaceutical composition comprising an anti-ghrelin monoclonal antibody or antigen-binding portion thereof of the present invention can be administered to a subject at risk for or exhibiting pathologies associated with obesity or related disorders as described herein using standard administration techniques, including oral, intravenous, intraperitoneal, subcutaneous, pulmonary, transdermal, intramuscular, intranasal, buccal, sublingual, or suppository administration.

A therapeutically-effective amount is at least the minimal dose, but less than a toxic dose, of an active agent which is necessary to impart therapeutic benefit to a subject. Stated another way, a therapeutically-effective amount is an amount which induces, ameliorates, or otherwise causes an improvement in the obese state of the mammal, e.g., by decreasing body mass index (BMI).

The route of administration of an antibody or antigen-binding portion thereof of the present invention may be oral, parenteral, by inhalation, or topical. Preferably, the molecules of the invention can be incorporated into a pharmaceutical composition suitable for parenteral administration. The term parenteral as used herein includes intravenous, intramuscular, subcutaneous, rectal, vaginal, or intraperitoneal administration. Peripheral systemic delivery by intravenous or intraperitoneal or subcutaneous injection is preferred. Suitable vehicles for such injections are straightforward.

The pharmaceutical composition typically must be sterile and stable under the conditions of manufacture and storage in the container provided, including e.g., a sealed vial or syringe. Therefore, pharmaceutical compositions may be sterile filtered after making the formulation, or otherwise made microbiologically acceptable. A typical composition for intravenous infusion could have a volume of as much as 250-1000 mL of fluid, such as sterile Ringer's solution, physiological saline, dextrose solution, and Hank's solution, and a therapeutically effective dose (e.g., 1 to 100 mg/mL, or more) of antibody or active fragment in an appropriate concentration. Therapeutic agents of the invention may be frozen or lyophilized for storage and reconstituted in a suitable sterile carrier prior to use. Lyophilization and reconstitution can lead to varying degrees of antibody activity loss (e.g., with conventional immunoglobulins, IgM antibodies tend to have greater activity loss than IgG antibodies). Dosages may have to be adjusted to compensate. Generally, a pH between 6 and 8 is preferred.

As is well known in the medical arts, dosages for any one subject depend upon many factors, including the patient's size, body surface area, age, severity of disease, the particular compound to be administered, sex, time and route of administration, general health, and other drugs being administered concurrently. A typical dose for an antibody or antigen-binding portion thereof of the present invention can be, for example, in the range of about 0.001 to about 1000 µg; however, doses below or above this exemplary range are envisioned, especially considering the aforementioned factors. The daily parenteral dosage regimen is about 0.1 µg/kg to about 100 mg/kg of total body weight, preferably from about 0.3 µg/kg to about 10 mg/kg, more preferably from about 1 µg/kg to about 1 mg/kg, and even more preferably from about 0.5 to about 10 mg/kg body weight per day. Progress can be monitored by periodic assessment, and doses adjusted accordingly.

As used herein, the terms "treatment," "treating," and the like refer to obtaining a desired pharmacologic and/or physiologic effect. The effect may be prophylactic in terms of completely or partially preventing a disease or symptom thereof, and/or may be therapeutic in terms of a partial or complete cure for a disease and/or adverse effect attributable to the disease. "Treatment" as used herein includes administration of a compound of the present invention for treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease or disorder or alleviating symptoms or complications thereof. Treatment may be in conjunction with behavior modification such as limitation of food intake and exercise. Treating obesity therefore includes inhibition of food intake, inhibition of weight gain, and/or inducing weight loss in subjects in need thereof.

A pharmaceutical composition of the invention preferably is, or contains, a "therapeutically effective amount" or a "prophylactically effective amount" of an antibody or antigen-binding portion thereof of the present invention. A "therapeutically effective amount" refers to an amount effective, at dosages and for periods of time necessary, to achieve the desired therapeutic result. A therapeutically effective amount of the antibody or antigen-binding portion thereof may vary according to factors such as the disease state, age, sex, and weight of the individual, and the ability of the antibody or antibody portion to elicit a desired therapeutic response in the individual. A therapeutically effective amount is also one in which any toxic or detrimental effect of the antibody is outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens can be adjusted to provide the optimum desired response (e.g., a therapeutic or prophylactic response). For example, a single bolus can be administered, several divided doses can be administered over time, or the dose can be proportionally reduced or increased as indicated by the exigencies of the therapeutic situation.

Given their ability to bind to ghrelin from multiple species, antibodies or antigen-binding portions thereof of the present invention can be used to detect, for example, rat or human ghrelin peptides in a biological sample, such as serum or plasma, using a conventional immunoassay, such as an enzyme linked immunosorbent assays (ELISA), a radioimmunoassay (RIA), or tissue immunohistochemistry. The invention provides a method for detecting ghrelin in a biological sample comprising contacting a biological sample with an antibody, or antigen-binding portion thereof, of the invention, and detecting either the antibody (or antibody portion) bound to ghrelin, or unbound antibody (or antibody portion), to thereby detect ghrelin in the biological sample. The antibody or portion thereof is directly or indirectly labeled with a detectable substance to facilitate detection of the bound or unbound antibody. Suitable detectable substances include various enzymes, prosthetic groups, fluorescent materials, luminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride, or phycoerythrin; an example of a luminescent material includes luminol; and examples of a radioactive material include $^{125}$I, $^{131}$I, $^{35}$S, or $^{3}$H.

Ghrelin can be assayed in biological fluids by a competition immunoassay utilizing ghrelin standards labeled with a detectable substance and an unlabeled anti-ghrelin monoclonal antibody or antigen-binding portion thereof. In this assay, the biological sample, the labeled ghrelin standards, and the anti-ghrelin monoclonal antibody or antigen-binding portion thereof of the invention are combined, and the amount of labeled ghrelin standard bound to the unlabeled antibody or portion thereof is determined. The amount of ghrelin in the sample is inversely proportional to the amount of labeled ghrelin standard bound to the anti-ghrelin monoclonal antibody or antigen-binding portion thereof.

An anti-ghrelin antibody or antigen-binding portion thereof of the present invention can be used in a diagnostic assay for ghrelin levels. Various diagnostic assay techniques known in the art can be used, such as competitive binding assays, direct or indirect ELISA sandwich assays, and immunoprecipitation assays conducted in either heterogeneous or homogeneous phases. See, e.g., Zola, *Monoclonal Antibodies: A Manual of Techniques*, CRC Press, Inc. (1987) pp. 147-158. The antibody or portion thereof used in the assay can be labeled with a detectable moiety. The detectable moiety should be capable of producing, either directly or indirectly, a detectable signal. For example, the detectable moiety can be a radioisotope, such as $^{3}$H, $^{14}$C, $^{32}$P, $^{35}$S, or $^{125}$I, a fluorescent or chemiluminescent compound (such as fluorescein isothiocyanate, rhodamine, or luciferin), or an enzyme (such as alkaline phosphatase, β-galactosidase or horseradish peroxidase). Any method known in the art for conjugating the antibody or antigen-binding portion thereof to the detectable moiety can be employed.

The following examples are offered for illustrative purposes only, and are not intended to limit the scope of the present invention in any way.

EXAMPLE 1

KinExA Measurement of Kinetic Constants of Humanized, Affinity Matured C2 Anti-Ghrelin Fabs The KinExA 3000 instrument, manufactured by Sapidyne, is used to measure binding kinetics. Briefly, streptavidin is covalently coupled to azlactone beads. Biotinylated C8 acylated human ghrelin (1-28) is subsequently bound to these streptavidin beads. The binding of free anti-ghrelin Fab to the beads is detected on the instrument.

To measure $K_d$s, individual tubes containing a constant concentration of 20-100 pM of Fab with decreasing serially diluted C8 acylated human ghrelin (1-28) are incubated for 18 h at 20° C. in 0.1% BSA, PBS. A total of 13-15 tubes are used for each $K_d$ determination. For example, clone 4a1 is used at a constant concentration of 20 pM and individual tubes are incubated with 0-20 nM of ghrelin. Incubations for other Fabs are set in a similar manner. After incubation, free Fab in each equilibrated sample is determined on the KinExA 3000 instrument according to the manufacturer's instructions. $K_d$ values are determined using the KinExA 3000 software.

$K_d$s for several Fabs of the present invention determined by the method described above are shown in Table 5. "C2 chimeric" refers to a Fab containing the heavy chain and light chain variable regions of C2 murine Fab 1111 fused to human CH1 and CL domains, respectively.

TABLE 5

| $K_d$s of Humanized, Affinity Matured C2 Anti-Ghrelin Fabs Determined by KinExA | |
|---|---|
| Clone | $K_d$ (pM) |
| C2 chimeric | 1100 |
| 4a1 | 6.4 |
| 5a1 | 1 |
| 7a1 | 4.2 |
| 7b2 | 25.3 |

These data demonstrate that exemplary humanized, affinity matured Fabs of the present invention bind C8 acylated human ghrelin (1-28) with improved affinity, i.e., in the low pM range (1 to about 25 pM), compared to C2 murine Fab 1111 disclosed in PCT International Publication WO 2005/016951, reported therein as exhibiting a $K_d$ of 1.04±0.31 nM for full length, acylated human ghrelin.

In another experiment, the affinities ($K_d$s) for C8 acylated human ghrelin (1-28) of anti-ghrelin C2 murine Fab 1111 and a complete murine Mab comprising the Fab 1111 murine sequence are measured using the KinExA 3000 instrument, and compared. Briefly, 10 μg human C8 acylated ghrelin (1-28) is covalently coupled to 50 mg azlactone beads (Sapidyne). The binding of free anti-ghrelin C2 murine Fab 1111 to the beads is detected on the instrument using a CY5 labeled donkey anti-mouse IgG$_1$ H+L antibody or rabbit anti-mouse F(ab')$_2$ antibody (Jackson ImmunoResearch). The binding of free anti-ghrelin C2 Mab (complete murine sequence including Fab 1111) to the beads is detected on the instrument using a CY5 labeled goat anti-mouse Fc gamma antibody (Jackson ImmunoResearch). To measure $K_d$, individual tubes containing a constant concentration of 60-6000 pM of Fab or Mab with decreasing serially diluted human ghrelin are incubated for 2 h at 25° C. in 0.1% BSA, PBS. A total of 12-tubes are used for each experiment, and at least two experiments using different concentrations of Fab and Mab (in general, one concentration would be under $K_d$ controlled concentrations, the other would be under receptor controlled concentrations). For example, anti-ghrelin C2 murine Fab is used at a constant concentration of either 60, 600, or 6000 pM, and individual tubes are incubated with 0-60, 0-100, or 0-1000 nM of ghrelin, respectively. After the incubation, free Fab or Mab in each equilibrated sample is determined on the KinExA 3000 instrument according to the manufacturer's instructions. $K_d$ values are assessed using the KinEkA 3000 n-curve analysis software.

The results are shown in Table 6.

TABLE 6

| Fab or Mab | $K_d$ (nM) |
|---|---|
| Anti-ghrelin C2 Fab (Fab1111) vs. human C8 ghrelin | 1.03 |
| (95% Confidence Interval: 640 pM to 1.25 nM) | (n = 3) |
| Anti-ghrelin C2 Mab vs. human C8 ghrelin | 1.44 |
| (95% Confidence Interval: 180 pM to 4.6 nM) | (n = 2) |

These data demonstrate that there is no significant change in the affinity of C2 murine Fab 1111 for human C8 acylated ghrelin (1-28), as measured by KinExA, due to the addition of a murine constant domain to generate a full length antibody.

EXAMPLE 2

BIAcore® Measurement of Affinities of Humanized, Affinity Matured C2 Mabs

The affinity ($K_d$) of humanized C2 anti-ghrelin Mabs is measured using a BIAcore® 2000 instrument containing a CM5 sensor chip. The BIAcore® utilizes the optical properties of surface plasmon resonance to detect alterations in protein concentration of interacting molecules within a dextran biosensor matrix. Except where noted, all reagents and materials are purchased from BIAcore® AB (Uppsala, Sweden). All measurements are performed at about 25° C. All samples containing either rat or human ghrelin (full length, C8- or C10-acylated, or desacylated) and anti-ghrelin Fab or Mab are diluted in HBS-EP buffer (150 mM sodium chloride, 3 mM EDTA, 0.005% (w/v) surfactant P-20, and 10 mM HEPES, pH 7.4). A capture antibody, goat anti-mouse kappa (Southern Biotechnology, Inc), or goat anti-mouse Fc gamma (Jackson ImmunoResearch), is immobilized onto flow cells using amine-coupling chemistry. Flow cells (1-4) are activated for 7 minutes with a 1:1 mixture of 0.1 M N-hydroxysuccinimide and 0.1 M 3-(N,N-dimethylamino)propyl-N-ethylcarbodiimide at a flow rate of 10 µl/min. The capture antibody, for example goat anti-mouse kappa, is diluted to 30 µg/mL in 10 mM sodium acetate, pH 4.5, and manually injected over all four flow cells at a flow rate of 10 µL/min. The surface density is monitored, and additional capture antibody is injected as needed to each individual cell until all flow cells reach a surface density of 4500-5000 response units (RU). Surfaces are blocked with a seven minute injection of 1 M ethanolamine-HCl, pH 8.5(10 µL/min). To ensure complete removal of any noncovalently bound capture antibody, 15 µL of 10 mM glycine, pH 1.5, are injected twice. Running buffer for kinetic experiments is HBS-EP buffer (150 mM sodium chloride, 3 mM EDTA, 0.005% (w/v) surfactant P-20, and 10 mM HEPES, pH 7.4). For C2_4A1, 5A1, and 7A1, the antibody is directly coupled to a CM5 chip using the amine-coupling chemistry described above, aiming for a surface density of between 800-1000 RU.

Collection of kinetic binding data is performed at maximum flow rate (100 µL/min) and a low surface density to minimize mass transport effects. Each analysis cycle consists of: (i) capture of 300-350 RU of Fabs or 850-950 RU of Mabs by injection of 5-10 µL of a 5-50 µg/ml solution over flow cell 2, 3 or 4 at a flow rate of 10 µL/min., (this step is not used in the case of C2_4A1, 5A1, and 7A1); (ii) 200 µL injection (2 min) of ghrelin (concentration range of 50 nM to 0.39 nM in 2-fold dilution increments) over all four flow cells with flow cell 1 as the reference flow cell; (iii) 20 min dissociation (buffer only flow); (iv) regeneration of chip surface with a 15 sec injection of 10 mM glycine, pH 1.5; and (v) a 2 min stabilization time before the start of the next cycle. The signal is monitored as flow cell 2 minus flow cell 1, flow cell 3 minus flow cell 1, and flow cell 4 minus flow cell 1. Samples and a buffer blank are injected in duplicate in a random order. Data are processed using BIAevaluation v.4.1 software and data are fit to a 1:1 binding model in either BIAevaluation v.4.1 or CLAMP global analysis software.

The results are shown in Table 7, with standard deviations calculated using the standard deviation function in Excel. All listed ghrelins are 28 amino acids in length.

TABLE 7

$K_d$s of Humanized, Affinity Matured C2 Anti-Ghrelin Mabs Determined by BIAcore ®

| Fab 1111[a‡] vs | $k_{on}$ (1/Ms) | $k_{off}$ (1/s) | $K_d$ (pM) | n |
|---|---|---|---|---|
| Human C8 ghrelin | $1.7 \times 10^6$ ($\pm 3.2 \times 10^5$) | $1.6 \times 10^{-3}$ ($\pm 1.2 \times 10^{-4}$) | 953 ($\pm 258$) | 8 |
| Rat C8 ghrelin | $1.4 \times 10^6$ ($\pm 2.6 \times 10^5$) | $1.6 \times 10^{-3}$ ($\pm 9.3 \times 10^{-5}$) | 1230 ($\pm 315$) | 5 |
| Human C10 ghrelin | $2.1 \times 10^6$ ($\pm 1.3 \times 10^5$) | $8.8 \times 10^{-3}$ ($\pm 1 \times 10^{-3}$) | 4550 ($\pm 3790$) | 3 |

[a]full murine sequence
[‡]Fab captured using a goat anti-mouse kappa antibody directly coupled to a CM5 chip.

| Mab C2[1*] vs | $k_{on}$ (1/MS) | $k_{off}$ (1/s) | $K_d$ (pM) | n |
|---|---|---|---|---|
| Human C8 ghrelin | $2.4 \times 10^6$ ($\pm 1.3 \times 10^6$) | $1.5 \times 10^{-3}$ ($\pm 4.9 \times 10^{-4}$) | 779 ($\pm 32$) | 11 |
| Rat C8 ghrelin | $8.0 \times 10^5$ ($\pm 3.7 \times 10^5$) | $1.8 \times 10^{-3}$ ($\pm 3.4 \times 10^{-4}$) | 2600 ($\pm 1140$) | 7 |
| Human C10 ghrelin | $1.9 \times 10^6$ ($\pm 9.8 \times 10^5$) | $9.2 \times 10^{-3}$ ($\pm 2.7 \times 10^{-3}$) | 4100 ($\pm 920$) | 6 |

[1]full murine sequence, i.e., Fab 1111 $V_H/V_L$ and murine Fc
*Mab captured using either goat anti-mouse kappa or goat anti-mouse Fc gamma antibody directly coupled to a CM5 chip.

| Mab C2[2†] vs | $k_{on}$ (1/Ms) | $k_{off}$ (1/s) | $K_d$ (pM) | n |
|---|---|---|---|---|
| Human C8 ghrelin | $7.4 \times 10^6$ ($\pm 4.1 \times 10^6$) | $2.8 \times 10^{-3}$ ($\pm 8.3 \times 10^{-4}$) | 363 ($\pm 6$) | 2 |
| Rat C8 ghrelin | $3.3 \times 10^6$ ($\pm 1.5 \times 10^6$) | $1.9 \times 10^{-3}$ ($\pm 2.2 \times 10^{-4}$) | 687 ($\pm 390$) | 2 |

[2]Murine $V_H/V_L$ Fab 1111 sequences with rat Fc chimera
[†]Mab directly coupled to the CM5 chip using amine coupling chemistry

| Mab C2_4A1[3†] vs | $k_{on}$(1/Ms) | $k_{off}$(1/s) | $K_d$ (pM) | n |
|---|---|---|---|---|
| Human C8 ghrelin | $1.6 \times 10^7$ ($\pm 5.6 \times 10^6$) | $1.4 \times 10^{-4}$ ($\pm 2.6 \times 10^{-5}$) | 10 ($\pm 5$) | 2 |
| Rat C8 ghrelin | $7.5 \times 10^6$ ($\pm 5 \times 10^6$) | $1.2 \times 10^{-4}$ ($\pm 5.8 \times 10^{-5}$) | 18 ($\pm 5$) | 2 |

[3]Human $V_H/V_L$ with rat Fc chimera
[†]Mab directly coupled to the CM5 chip using amine coupling chemistry

| Mab C2_5A1[3†] vs | $k_{on}$ (1/Ms) | $k_{off}$ (1/s) | $K_d$ (pM) | n |
|---|---|---|---|---|
| Human C8 ghrelin | $8.6 \times 10^6$ ($\pm 1 \times 10^6$) | $1.2 \times 10^{-4}$ ($\pm 2.6 \times 10^{-5}$) | 13 ($\pm 2$) | 2 |

TABLE 7-continued

K$_d$s of Humanized, Affinity Matured C2 Anti-Ghrelin
Mabs Determined by BIAcore ®

| Rat C8 ghrelin | $6.6 \times 10^6$ ($\pm 2.8 \times 10^6$) | $1.2 \times 10^{-4}$ ($\pm 2.5 \times 10^{-5}$) | 20 ($\pm 5$) | 2 |

[3] Human V$_H$/V$_L$ with rat Fc chimera
[†] Mab directly coupled to the CM5 chip using amine coupling chemistry

| Mab C2_7A1[3†] vs | k$_{on}$ (1/Ms) | k$_{off}$ (1/s) | K$_d$ (pM) | n |
|---|---|---|---|---|
| Human C8 ghrelin | $1.0 \times 10^7$ ($\pm 4.4 \times 10^6$) | $1.3 \times 10^{-4}$ ($\pm 8.4 \times 10^{-5}$) | 12 ($\pm 3$) | 2 |

[2] Human V$_H$/V$_L$ with rat Fc chimera
[†] Mab directly coupled to the CM5 chip using amine coupling chemistry.

These data demonstrate that representative humanized, affinity matured antibodies of the present invention have a higher affinity (lower K$_d$) for C8-acylated human and rat ghrelin than C2 murine Fab 1111. None of the listed Mabs has any apparent affinity for desacylated human ghrelin (data not shown).

Taken in conjunction with the data in Tables 5 and 6 of Example 1, one can conclude that humanized, affinity matured Fabs and Mabs of the present invention exhibit significantly superior binding to human C8 ghrelin compared to C2 murine Fab 1111. Furthermore, these improved binding kinetics are not due to the addition of a constant region (human, mouse, or rat) as suggested by the similarity in affinity between the presently improved Fabs and Mabs (Tables 5-6 and 7, respectively).

EXAMPLE 3

Effect of Humanized, Affinity Matured C2 5a1 Antibody On Food Consumption in Rats This study is designed to determine if pretreatment of rats with a humanized C2 antibody specific for acylated human ghrelin (1-28) as disclosed herein can attenuate the increase in food consumption resulting from acute, subcutaneous administration of acylated human ghrelin.

Twenty to twenty-one day old male, Long-Evans weanling rats (Harlan Sprague-Dawley, Indianapolis, Ind.) are fed a calorie dense TD95217 diet (Harlan Teklad, Ind.) ad libtium upon arrival in the laboratory. Rats are acclimated for two weeks at a temperature of 26° C. and a 12:12 hour light:dark cycle (lights on from 7:00-19:00 hours).

On the first day of each of the two studies, animals are randomized into three groups, each containing 24 rats. (Different groups of rats are used in each experiment). In each experiment, two groups are injected subcutaneously with control (isotype) antibody, and one group is injected subcutaneously with either humanized, affinity matured V$_H$/V$_L$ (Fab C2_5a1 sequences) with rat Fc chimeric C2 anti-ghrelin antibody (FIG. 1, Panel A), or murine V$_H$/V$_L$ (Fab 1111 sequences) with rat Fc chimeric C2 antibody (FIG. 1, Panel B) at 1 PM (13:00 hours) at a dose of 10 mg/kg. All injections are in a volume of 1 mL/kg body weight using a saline vehicle. Forty-eight hours after antibody administration, rats are treated with saline vehicle or C8 acylated human ghrelin (1-28) (1 mg/kg s.c.) in a 1 mL/kg volume. One of the isotype control pretreated groups and the C2-type antibody pretreated groups receive C8 acylated human ghrelin, while one of the isotype control pretreated groups receives saline. The treatment groups are thus:

Group 1: Control isotype antibody+saline (n=24);
Group 2: Control isotype antibody+C8 human ghrelin (n=24); and
Group 3: Anti-ghrelin C2-type antibody+C8 human ghrelin (n=24)

After ghrelin or vehicle injection, rats are placed in individual cages with free access to TD95217 chow and water. Cumulative food consumption is monitored at 30 minutes and 60 minutes post-ghrelin or saline injection. The amount of food consumed by each group of rats is compared using One-Way ANOVA (Newman-Keuls) statistics, and a probability less than or equal to 0.05 is considered significant.

Results are shown in FIG. 1, Panels A (humanized C2_5a1 antibody sequences) and B (C2 murine Fab 1111 antibody sequences), as bar graphs showing the mean grams of food consumed by each group at the 30 and 60 minute time points and the standard errors of the means (SEM). Asterisks indicate the following significant differences:

Panel A: P<0.05 ANOVA SNK vs. saline and C2_5a1 antibody;
Panel B: P<0.05 ANOVA SNK vs. saline The data demonstrate that in this rat model, preadministration of the C2_5a1 antibody containing humanized, affinity matured V$_H$/V$_L$ with rat Fc exhibiting a K$_d$ for C8 acylated human ghrelin (1-28) of 13 pM (note Table 7) is more effective than the murine V$_H$/V$_L$ (Fab 1111 sequences) with rat Fc chimeric C2 antibody, exhibiting a K$_d$ of 363 pM for C8 acylated human ghrelin (Table 7), in reducing food consumption after administration of acylated human ghrelin (1-28).

The invention being thus described, it is obvious that the same can be varied in many ways. Such variations are not to be regarded as a departure from the spirit and scope of the present invention, and all such modifications as would be obvious to one skilled in the art are intended to be included within the scope of the following claims.

We claim:

1. An antibody, or antigen-binding portion thereof, which binds acylated human ghrelin, wherein
    each light chain variable region comprises a peptide with the amino acid sequence shown in SEQ ID NO:34 and each heavy chain variable region comprises a peptide with the amino acid sequence shown in SEQ ID NO:35.

2. The antibody or an antigen-binding portion thereof of claim 1, comprising a human constant region.

3. A pharmaceutical composition, comprising said antibody or an antigen-binding portion thereof of claim 1, and a pharmaceutically acceptable carrier, diluent, or excipient.

4. A method of treating obesity, morbid obesity, non-insulin dependent diabetes mellitus, Prader-Willi Syndrome, hyperphagia, or impaired satiety in a mammal, comprising administering to a mammal in need thereof an effective amount of said antibody or antigen-binding portion thereof of claim 1.

5. The method of claim 4, wherein said mammal is a human.

6. A method of reducing food intake in a patient, comprising administering to a patient in need thereof a therapeutically effective amount of an antibody or an antigen-binding portion thereof of claim 1.

7. The method of claim 6, wherein said patient is a human.

8. A pharmaceutical composition, comprising said antibody or antigen-binding portion thereof of claim 2, and a pharmaceutically acceptable carrier, diluent, or excipient.

9. A method of treating obesity, morbid obesity, non-insulin dependent diabetes mellitus, Prader-Willi Syndrome, hyperphagia, or impaired satiety in a mammal, comprising administering to a mammal in need thereof an effective amount of said antibody or antigen-binding portion thereof of claim 2.

10. The method of claim 9, wherein said mammal is a human.

11. A method of reducing food intake in a patient, comprising administering to a patient in need thereof a therapeutically effective amount of an antibody or antigen-binding portion thereof of claim 2.

12. The method of claim 11, wherein said patient is a human.

* * * * *